(12) United States Patent
Roschin et al.

(10) Patent No.: US 12,376,944 B2
(45) Date of Patent: *Aug. 5, 2025

(54) AUTOMATIC APPLICATION OF DOCTOR'S PREFERENCES WORKFLOW USING STATISTICAL PREFERENCE ANALYSIS

(71) Applicant: Align Technology, Inc., San Jose, CA (US)

(72) Inventors: Roman A. Roschin, Moscow (RU); Evgenii Vladimirovich Karnygin, Moscow (RU); Dmitry Kirsanov, Moscow (RU); Grigoriy Yazykov, Balashikha (RU); Ilfat Sabirov, Zelenodolsk (RU); Ruslan Matvienko, Moscow (RU); Vasily Paraketsov, Moscow (RU)

(73) Assignee: Align Technology, Inc., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/536,204

(22) Filed: Dec. 11, 2023

(65) Prior Publication Data

US 2024/0115352 A1  Apr. 11, 2024

Related U.S. Application Data

(63) Continuation of application No. 16/826,036, filed on Mar. 20, 2020, now Pat. No. 12,048,604.

(60) Provisional application No. 62/821,825, filed on Mar. 21, 2019, provisional application No. 62/821,858, filed on Mar. 21, 2019.

(51) Int. Cl.
*A61C 7/00* (2006.01)
*A61C 9/00* (2006.01)
*G06F 40/10* (2020.01)

(52) U.S. Cl.
CPC .......... *A61C 7/002* (2013.01); *A61C 9/0046* (2013.01); *G06F 40/10* (2020.01)

(58) Field of Classification Search
CPC ........ A61C 7/002; A61C 9/0046; G06F 40/10
USPC ....................................................... 433/24
See application file for complete search history.

(56) References Cited

U.S. PATENT DOCUMENTS

| | | |
|---|---|---|
| 6,227,850 B1 | 5/2001 | Chishti et al. |
| 6,227,851 B1 | 5/2001 | Chishti et al. |
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,621,491 B1 | 9/2003 | Baumrind et al. |
| 6,688,886 B2 | 2/2004 | Hughes et al. |

(Continued)

FOREIGN PATENT DOCUMENTS

CN     108630310 A    10/2018

*Primary Examiner* — Matthew M Nelson
(74) *Attorney, Agent, or Firm* — Shay Glenn LLP

(57) ABSTRACT

Methods and apparatuses for automatic treatment planning, including recommendation systems, quality assurance, error prevention, text mining, text matching, and treatment planning optimization.

24 Claims, 16 Drawing Sheets

(56) References Cited

U.S. PATENT DOCUMENTS

| | | |
|---|---|---|
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,942,672 B2 | 5/2011 | Kuo |
| 7,970,627 B2 | 6/2011 | Kuo et al. |
| 7,970,628 B2 | 6/2011 | Kuo et al. |
| 7,987,099 B2 * | 7/2011 | Kuo ................. G16H 50/70 705/2 |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,469,705 B2 * | 6/2013 | Sachdeva ............. G16H 50/50 433/24 |
| 8,562,338 B2 | 10/2013 | Kitching et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,642,678 B2 | 5/2017 | Kuo |
| 10,242,157 B1 * | 3/2019 | Suda ................. G16H 40/20 |
| 10,248,883 B2 | 4/2019 | Borovinskih et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 11,154,381 B2 | 10/2021 | Roschin et al. |
| 11,259,896 B2 | 3/2022 | Matov et al. |
| 11,357,598 B2 | 6/2022 | Cramer |
| 11,395,717 B2 | 7/2022 | Yuryev et al. |
| 11,432,908 B2 | 9/2022 | Kopelman et al. |
| 11,464,604 B2 | 10/2022 | Makarenkova et al. |
| 11,478,334 B2 | 10/2022 | Matov et al. |
| 11,484,389 B2 | 11/2022 | Sterental et al. |
| 11,534,272 B2 | 12/2022 | Li et al. |
| 11,553,988 B2 | 1/2023 | Mednikov et al. |
| 11,633,268 B2 | 4/2023 | Moalem et al. |
| 11,642,195 B2 | 5/2023 | Gao et al. |
| 11,651,494 B2 | 5/2023 | Comito et al. |
| 11,654,001 B2 | 5/2023 | Roschin et al. |
| 11,707,344 B2 | 7/2023 | Roschin et al. |
| 11,810,271 B2 | 11/2023 | Shi et al. |
| 11,850,111 B2 | 12/2023 | Derakhshan et al. |
| 2002/0006597 A1 | 1/2002 | Andreiko et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0010450 A1 | 1/2005 | Hultgren et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2007/0003900 A1 * | 1/2007 | Miller ................. A61C 7/00 433/24 |
| 2007/0238065 A1 * | 10/2007 | Sherwood ............ A61C 7/08 433/24 |
| 2008/0305454 A1 * | 12/2008 | Kitching ............. A61C 7/00 433/24 |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0092907 A1 | 4/2010 | Knopp |
| 2010/0151404 A1 * | 6/2010 | Wu .................... A61C 7/00 433/24 |
| 2010/0167243 A1 | 7/2010 | Spiridonov et al. |
| 2013/0204599 A1 | 8/2013 | Matov et al. |
| 2014/0122027 A1 * | 5/2014 | Andreiko ............ A61B 1/24 703/1 |
| 2014/0324919 A1 | 10/2014 | Badawi |
| 2016/0038092 A1 * | 2/2016 | Golay ................ A61C 8/00 600/408 |
| 2017/0100213 A1 * | 4/2017 | Kuo .................. G16H 20/40 |
| 2017/0273760 A1 | 9/2017 | Morton et al. |
| 2017/0296303 A1 * | 10/2017 | Tod ................... G16H 20/40 |
| 2018/0280118 A1 | 10/2018 | Cramer |
| 2018/0293354 A1 * | 10/2018 | Dejori ................ G16H 50/20 |
| 2019/0043607 A1 * | 2/2019 | Sears ................. G16H 30/20 |
| 2019/0175303 A1 * | 6/2019 | Akopov .............. A61C 7/002 |
| 2020/0155274 A1 | 5/2020 | Pimenov et al. |
| 2020/0297458 A1 * | 9/2020 | Roschin .............. G06F 40/10 |
| 2020/0306011 A1 | 10/2020 | Chekhonin et al. |
| 2021/0134436 A1 | 5/2021 | Meyer et al. |
| 2021/0244502 A1 * | 8/2021 | Farkash .............. A61B 5/0077 |
| 2021/0401546 A1 * | 12/2021 | Gardner ............. A61C 7/002 |
| 2022/0061958 A1 * | 3/2022 | Savard ............... G16H 30/40 |

* cited by examiner

|  | Number of cases | Percent of all |
|---|---|---|
| All cases | 1506 | 100 % |
| Initial cases with recognized text instructions | 916 | 60.82 % |
| Automatically applied treatment options remain in accepted cases (positive scenario) | 880 | 58.43% |
| No treatment options were automatically applied and none of them were applied manually (positive scenario) | 536 | 35.59% |
| Automatically applied treatment options were changed in accepted cases (negative scenario) | 36 | 2.39% |
| No treatment options were automatically applied but some of them were applied manually (neutral scenario) | 54 | 3.59% |

FIG. 5

| User ID | Positive cases number | Positive cases in percent of all | Negative cases number | Negative cases in percent of all | Neutral cases number | Neutral cases in percent of all | Overall cases number |
|---|---|---|---|---|---|---|---|
| Doctor A | 6 | 100 % | 0 | 0 % | 0 | 0 % | 6 |
| Doctor B | 36 | 97.3 % | 1 | 2.7 % | 0 | 0 % | 37 |
| Doctor C | 20 | 100 % | 0 | 0 % | 0 | 0 % | 20 |
| Doctor D | 16 | 100 % | 0 | 0 % | 0 | 0 % | 16 |
| Doctor E | 39 | 90.7 % | 3 | 7.0 % | 1 | 2.3 % | 43 |
| Doctor F | 14 | 100 % | 0 | 0 % | 0 | 0 % | 14 |

FIG. 6

| DoctorID | Preference text | Decision | Clinical behavior |
|---|---|---|---|
| DoctorW | "Please set up aligner 2 to ext 1.4.2.4.3.4.4.4.only" | Decline | |
| DoctorX | "all are extracted between 2 and 3 stage" | Accept | Perform extractions at the stage 3 |
| DoctorY | "extractions always after stage 3" | Accept | Perform extractions at the stage 4 |
| DoctorZ | Do the extraction at stage 2 | Accept | Perform extractions at the stage 2 |

| Reference | Found text | Similarity |
|---|---|---|
| -IPR no antes de la etapa 2 | No ipr antes de la etapa 3 | 100 % |
| Please space ALL of our IPR appointments starting at stage 12, 24, 36, etc | space ALL of our ipr appointments starting at stage 0,11, 22, 33 etc | 94 % |
| IPR after 3rd aligner if needed | ipr after 3rd aligner | 81 % |
| Place all attachments on aligner 3 | Place attachments and do ipr on the 3rd aligner | 76 % |

FIG. 11

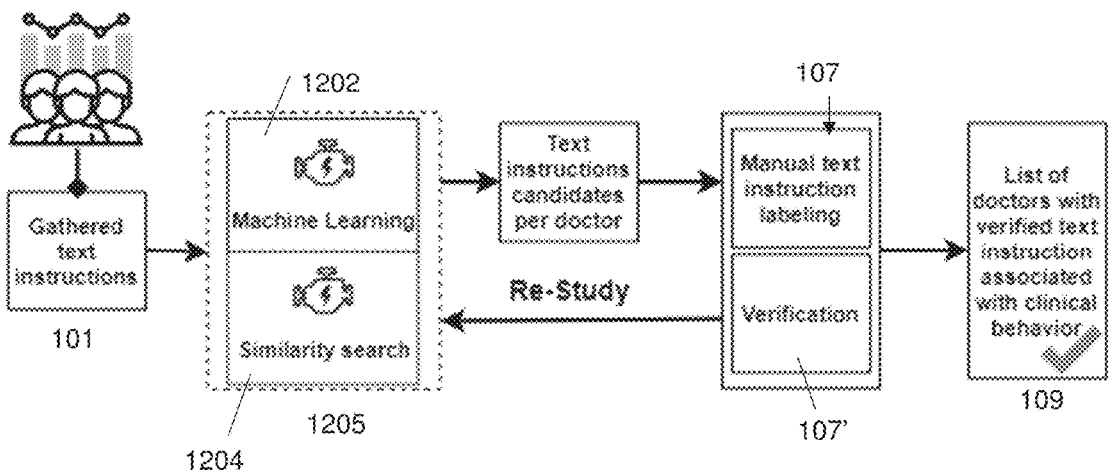

FIG. 12

| ID | Matched text instruction | Reference text | Decision | Clinical behavior |
|---|---|---|---|---|
| DoctorW | Place all attachments on aligner 3 | Place attachments and do ipr on the 3rd aligner | Accept | Place attachments at stage 3 |
| DoctorX | *Place attachments at tray 1 | tray 6, PLACE attachments, start ipr | Accept | Place attachments at stage 1 |
| DoctorY | IPR after 3rd aligner if needed | ipr after 3rd aligner | Accept | Perform IPR after stage 3 |
| DoctorZ | at aligner 1 | do ipr at aligners #5 | Decline | - |

FIG. 13

No attachments in overcorrection aligners

Remove attachments at overcorrection

To make first sentence from second we must perform:
- 3 substitutions
- 9 insertions (eight letters plus one space)
- 4 deletions
- 1 transposition $$Similarity = \left(1 - \frac{N_{operations}}{\max(L_1, L_2)}\right) \times 100\% = \left(\frac{N_{match}}{\max(L_1, L_2)}\right) \times 100\%$$

FIG. 14

AUTOMATIC APPLICATION OF DOCTOR'S PREFERENCES WORKFLOW USING STATISTICAL PREFERENCE ANALYSIS

CROSS REFERENCE TO RELATED APPLICATIONS

This application is a continuation of U.S. patent application Ser. No. 16/826,036, titled "AUTOMATIC APPLICATION OF DOCTOR'S PREFERENCES WORKFLOW USING STATISTICAL PREFERENCE ANALYSIS," filed on Mar. 20, 2020, now U.S. Patent No. 12,048,604, which claims priority to U.S. Provisional Patent Application No. 62/821,825, titled "AUTOMATIC APPLICATION OF DOCTOR'S PREFERENCES WORKFLOW," filed on Mar. 21, 2019, and to U.S. Provisional Patent Application No. 62/821,858, titled "AUTOMATIC APPLICATION OF DOCTOR'S PREFERENCES WORKFLOW USING STATISTICAL PREFERENCE ANALYSIS," filed on Mar. 21, 2019, each of which are herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Methods and apparatuses for orthodontic treatment planning

BACKGROUND

Orthodontic and dental treatments using a series of patient-removable appliances (e.g., orthodontic aligners, palatal expanders, etc.) are very useful for treating patients, and in particular for treating malocclusions. Treatment planning is typically performed in conjunction with the dental professional (e.g., dentist, orthodontist, dental technician, etc., referred to herein as "users"), by generating a model of the patient's teeth in a final configuration and then breaking the treatment plan into a number of intermediate stages (steps) corresponding to individual appliances that are worn sequentially. This process may be interactive, adjusting the staging and in some cases the final target position, based on constraints on the movement of the teeth and the dental professional's preferences. Once the final treatment plan is finalized, the series of aligners may be manufactured corresponding to the treatment planning.

This treatment planning process may include many manual steps that are complex and may require a high level of knowledge of orthodontic norms. Further, because the steps are performed in series, the process may require a substantial amount of time. Manual steps may include preparation of the model for digital planning, reviewing and modifying proposed treatment plans (including staging) and aligner features placement (which includes features placed either on a tooth or on an aligner itself). These steps may be performed before providing an initial treatment plan to a dental professional, who may then modify the plan further and send it back for additional processing to adjust the treatment plan, repeating (iterating) this process until a final treatment plan is completed and then provided to the patient.

Existing systems and methods for treatment planning may be time consuming, and may provide only limited choices and control to the dental professional.

SUMMARY OF THE DISCLOSURE

The systems, methods, and/or computer-readable media described herein provide technical solutions to the highly technical problems of orthodontic treatment planning Generally, these methods may include creating and modifying, e.g., updating, a collection of user (e.g., physician, dentist, orthodontist, etc.) or user group preferences and using these user or user group preferences to automatically create and/or modify an orthodontic treatment plan.

Many dental doctors have strong clinical preferences, which should be applied to majority of treatment case. These preferences can be defined by doctor once on the doctor's personal account or repeatedly passed through instructions, specified for each patient. For example, 'remove attachments at the end of treatment' is a very common instruction used by large amount of doctors. This kind of text instructions have impact to treatment case processing time duration, because technicians have to spend time for reading, implementing and re-checking well-known and common instructions.

Described herein are methods of creating and/or modifying a treatment plan by automatically detecting user preferences, e.g., clinical preferences, and incorporating these preferences into a treatment plan for approval by the user; this treatment plan may be finalized and used to produce one or a series of orthodontic appliances to treat a patient. Also described herein are treatment planning engines that may perform any of these methods.

A treatment planning engine may use the collection of user or user group preferences, along information about the patient's oral cavity (such as a scan of the patient's teeth) to automatically generate one or more treatment plans specific to the patient. The collection of user or user group preferences may be a data structure (e.g., data store, date base, etc.) that is accessed and/or modified by one or more treatment planning engines. The treatment planning engine may include or may access a preference engine that may create, modify, update and/or distribute the collection of user or user group preferences.

Because the treatment plan(s) is/are generated using user or user-group specific information by the treatment planning engine, the treatment planning engine may automatically generate treatment plans customized to a patient that are also customized to or for the user. The resulting treatment plans may be reviewed and approved by the user; any modifications to the automatically generated treatment plans may be used by the treatment planning engine and/or the preference engine to update and/or modify the collection of user or user group preferences.

As used herein, an orthodontic treatment plan (or simply a "treatment plan") may refer to a series of steps, devices and/or schedules for altering a subject's dental arch to achieve or approach a desired outcome. A treatment plan may identify or described one or more dental appliances (including dental appliances such as, but not limited to, aligners) that may be used to alter the subject's dental arch. The treatment plan may also or alternatively include steps for modifying the subject's dental arch, both with and/or without one or more dental appliances. The treatment plan may be sequential, e.g., indicating multiple treatment steps, some or all of which may include an orthodontic treatment appliance such as a dental appliance. In some variations the treatment plan may include preparing the subject's dental arch (e.g., by extracting, shaping, trimming, or otherwise altering one or more of the subject's teeth). The treatment plan may indicate movement (and/or non-movement) of one or more of the patient's teeth, including indicating the timing or sequencing of movements (start, duration, finishing). A treatment plan may include steps for designing and/or fabricating one or more (including an ordered series) of dental appliances. A treatment plan may include a schedule of dental appliances indicating the timing for wearing the one or more dental appliances.

Any of the methods or apparatuses (including software, hardware and firmware, such as a treatment planning engine) may receive a set of patients-specific information, such as a description (e.g., model, 3D scan, mold, etc.) of a patient dental arch, including all or part of the patient's upper and/or lower dental arches, as well as an indication of the user (e.g., orthodontist, dentist, doctor, dental technician, etc.) associated with the patient. In some variations, a description of user instructions for the patient may be provided. The user instructions may be a description of the user's general and/or specific preferences for a type or category of dental treatment(s) or they may be specific to the patient. User instructions may include, for example, tooth movement restrictions (e.g., indicating which teeth should not move as part of the treatment), if interproximal reduction (IPR) should be used, and/or how, when during treatment or where to perform IPR, if attachments should be used, where (e.g., on which teeth) attachments should be placed if used, changing spacing distance between teeth, extraction instructions including which teeth to extract and at which stage to extract them during treatment, leveling strategy (e.g., "align by incisal edge" or "align by gingiva margins"), etc. The user instructions may indicate any appropriate number of preferences/instructions, including one or more. Instructions may be categorical, and/or conditional (e.g., instructions that depend on one or more other conditions).

A treatment planning engine may refer to a software, hardware, and/or firmware (or some combination of these) that receives the treatment planning instructions and/or patient information (e.g., a digital model of the patient's teeth), and may apply the treatment planning instructions to the patient information to generate one or more treatment plans. Any appropriate digital model of a patient's teeth may be used, including a 3D volumetric scan, such as a scan from an intraoral scanner.

Described herein are methods of generating a treatment plan for an orthodontic treatment. Any of these methods may be computer-implemented methods. For example, described herein are computer-implemented methods comprising: creating a database of user preferences by: identifying a reference key preference text statement corresponding to a clinical behavior for treating a patient's teeth, accessing a collection of user-specific text instructions comprising a plurality of dental treatment instructions that are each associated with a specific user, identifying a user-specific textual key preference statement from the collection of user-specific text instructions by matching, within a specified probability range, the reference key preference text statement with a user-specific text instruction from the collection of user-specific text instructions, and adding, into the database of user preferences, an entry linking the user-specific textual key preference statement, the specific user associated with the user-specific textual key preference statement, and the clinical behavior for treating the patient's teeth; receiving a description of a patient's dentition; receiving patient treatment instructions from a dental professional for performing an orthodontic procedure on the patient; and automatically generating a dental treatment plan using the database of user preferences.

For example, a computer-implemented method may include: creating a database of user preferences by: identifying a reference key preference text statement corresponding to a clinical behavior for treating a patient's teeth, accessing a collection of user-specific text instructions comprising a plurality of dental treatment instructions that are each associated with a specific user, identifying a user-specific textual key preference statement from the collection of user-specific text instructions by using both a machine learning agent and similarity searching to match, within a specified probability range, the reference key preference text statement with a user-specific text instruction from the collection of user-specific text instructions, and adding, into the database of user preferences, an entry linking the user-specific textual key preference statement, the specific user associated with the user-specific textual key preference statement, and the clinical behavior for treating the patient's teeth; receiving a description of a patient's dentition; receiving patient treatment instructions from a dental professional for performing an orthodontic procedure on the patient; and automatically generating a dental treatment plan using the database of user preferences.

A computer-implemented method may comprise: creating a database of user preferences, wherein the database comprises a plurality of user identifiers, one or more user-specific textual key preferences corresponding to each user identifier, and a clinical behavior corresponding to each user-specific textual key preference; receiving a description of a patient's dentition; receiving user-specific textual instructions for performing an orthodontic procedure on the patient; and automatically generating a dental treatment plan by interpreting the user textual instructions using the database of user preferences to match one or more user-specific textual key preferences with one or more phrases in the user-specific textual instructions and incorporating the clinical behavior corresponding to each matching user-specific textual instructions in the dental treatment plan.

In any of these methods, automatically generating a dental treatment plan using the database of user preferences may comprise finding any user-specific textual key preference statement from the database of user preferences that are associated with the dental professional, and incorporating in the dental treatment plan the clinical behavior for treating the patient's teeth that corresponds to any found user-specific key preference which matches a phrase in the patient treatment instructions.

Any appropriate method for identifying the user-specific textual key preference statement from the collection of user-specific text instructions may be used, including using a machine learning agent to match the reference key preference text statement with the user-specific text instruction from the collection of user-specific text instructions. For example, any of these methods may include training the machine learning agent using a set of positive cases selected from the plurality of dental treatment instructions and a set of negative cases selected from the plurality of dental treatment instructions. The machine learning agent may be implementing a variation of bag of words adapted to analyze sentences. Identifying the user-specific textual key preference statement using the machine learning agent to match the reference key preference text statement with the user-specific text instruction from the collection of user-specific text instructions may further comprise using a similarity search concurrently with the machine-learning agent. For example, the similarity search may comprise a Damerau-Levenshtein distance measure. In any of these methods, identifying the user-specific textual key preference statement from the collection of user-specific text instructions may comprise using a similarity search agent to match the reference key preference text statement with the user-specific text instruction from the collection of user-specific text instructions.

Any of these methods may include gathering the collection of user-specific text instructions from a collection of historical treatment data. Receiving the description of a patient's dentition may comprise receiving a digital model of the patient's dentition.

Also described herein are systems that may perform any of the methods described herein. For example, a system may comprise: one or more processors; memory coupled to the one or more processors, the memory configured to store computer-program instructions, that, when executed by the one or more processors, perform a computer-implemented method comprising: creating a database of user preferences by: identifying a reference key preference text statement corresponding to a clinical behavior for treating a patient's teeth, accessing a collection of user-specific text instructions comprising a plurality of dental treatment instructions that are each associated with a specific user, identifying a user-specific textual key preference statement from the collection of user-specific text instructions by matching, within a specified probability range, the reference key preference text statement with a user-specific text instruction from the collection of user-specific text instructions, and adding, into the database of user preferences, an entry linking the user-specific textual key preference statement, the specific user associated with the user-specific textual key preference statement, and the clinical behavior for treating the patient's teeth; receiving a description of a patient's dentition; receiving patient treatment instructions from a dental professional for performing an orthodontic procedure on the patient; and automatically generating a dental treatment plan using the database of user preferences.

A system may comprise: one or more processors; memory coupled to the one or more processors, the memory configured to store computer-program instructions, that, when executed by the one or more processors, perform a computer-implemented method comprising: creating a database of user preferences by: identifying a reference key preference text statement corresponding to a clinical behavior for treating a patient's teeth, accessing a collection of user-specific text instructions comprising a plurality of dental treatment instructions that are each associated with a specific user, identifying a user-specific textual key preference statement from the collection of user-specific text instructions by using both a machine learning agent and similarity searching to match, within a specified probability range, the reference key preference text statement with a user-specific text instruction from the collection of user-specific text instructions, and adding, into the database of user preferences, an entry linking the user-specific textual key preference statement, the specific user associated with the user-specific textual key preference statement, and the clinical behavior for treating the patient's teeth; receiving a description of a patient's dentition; receiving patient treatment instructions from a dental professional for performing an orthodontic procedure on the patient; and automatically generating a dental treatment plan using the database of user preferences.

In some variations, a system may include: one or more processors; memory coupled to the one or more processors, the memory configured to store computer-program instructions, that, when executed by the one or more processors, perform a computer-implemented method comprising: creating a database of user preferences, wherein the database comprises a plurality of user identifiers, one or more user-specific textual key preferences corresponding to each user identifier, and a clinical behavior corresponding to each user-specific textual key preference; receiving a description of a patient's dentition; receiving user-specific textual instructions for performing an orthodontic procedure on the patient; and automatically generating a dental treatment plan by interpreting the user textual instructions using the database of user preferences to match one or more user-specific textual key preferences with one or more phrases in the user-specific textual instructions and incorporating the clinical behavior corresponding to each matching user-specific textual instructions in the dental treatment plan.

Also described herein are methods and apparatuses (e.g., systems) for that use statistical preference analysis. For example, a computer-implemented method may include: creating a database of user preferences by: performing a statistical preference analysis to identify, from a collection of user-specific text instructions comprising a plurality of dental treatment instructions that are each associated with a specific user, a key preference text statement and a corresponding clinical behavior for treating a patient's teeth associated with a single user, adding, into the database of user preferences, an entry linking the key preference text statement, the single user associated with the key preference text statement, and the corresponding clinical behavior for treating the patient's teeth; receiving a description of a patient's dentition; receiving patient treatment instructions from a dental professional for performing an orthodontic procedure on the patient; and automatically generating a dental treatment plan using the database of user preferences.

Performing the statistical preference analysis may comprise confirming that the clinical behavior for treating a patient's teeth remains approximately constant over a time period (e.g., remains constant over 70% of the time period, over 75% of the time period, over 80% of the time period, over 85% of the time period, over 90% of the time period, over 95% of the time period, etc.), where the time period may be the duration of a cluster of the most recent treatment plans.

For example, a computer-implemented method may include: creating a database of user preferences by: collecting user-specific text instructions comprising a plurality of dental treatment instructions that are each associated with a clinical dental procedure associated with a single user from a collection of historical treatment data; identifying, over a time period, a statistically consistent clinical behavior for treating the patient's teeth from the clinical dental procedure instructions and a corresponding key preference text statement; adding, into the database of user preferences, an entry linking the key preference text statement, the single user, and the corresponding clinical behavior for treating the patient's teeth; receiving a description of a patient's dentition; receiving patient treatment instructions from a dental professional for performing an orthodontic procedure on the patient; and automatically generating a dental treatment plan using the database of user preferences.

A computer-implemented method may include: creating a database of user preferences by: collecting user-specific text instructions comprising a plurality of dental treatment instructions that are each associated with a clinical dental procedure associated with a single user from a collection of historical treatment data; identifying, over the time period, a statistically consistent clinical behavior for treating the patient's teeth from the clinical dental procedure instructions and a corresponding key preference text statement, wherein the time period comprises the duration of a most recent cluster of the clinical behavior for treating the patient's teeth; adding, into the database of user preferences, an entry linking the key preference text statement, the single user, and the corresponding clinical behavior for treating the patient's teeth; receiving a description of a patient's dentition; receiving patient treatment instructions from a dental professional for performing an orthodontic procedure on the patient; and automatically generating a dental treatment plan using the database of user preferences.

Automatically generating a dental treatment plan using the database of user preferences may include finding any user-specific textual key preference statement from the database of user preferences that are associated with the dental professional, and incorporating in the dental treatment plan the clinical behavior for treating the patient's teeth that corresponds to any found user-specific key preference which matches a phrase in the patient treatment instructions.

The statistical preference analysis may comprise identifying the clinical behavior for treating the patient's teeth from the clinical dental procedure instructions and a corresponding key preference text statement, wherein the clinical behavior for treating the patient's teeth is a statistically consistent over a time period.

Any of these methods may include collecting, from a collection of historical treatment data, the user-specific text instructions comprising a plurality of dental treatment instructions, wherein each dental treatment instruction is associated with a clinical dental procedure associated with a single user.

Performing the statistical preference analysis may comprise performing the statistical preference analysis after limiting the statistical preference analysis to a time period after confirming that the clinical behavior for treating a patient's teeth is statistically consistent over a recent behavior detection.

Any of these methods may include manually verifying the key preference text statement and the corresponding clinical behavior for treating the patient's teeth prior to adding it to the database of user preferences. Receiving the description of the patient's dentition may comprise receiving a digital model of the patient's dentition.

Also described herein are system configured to perform any of the methods described herein. For example, a system may include: one or more processors; memory coupled to the one or more processors, the memory configured to store computer-program instructions, that, when executed by the one or more processors, perform a computer-implemented method comprising: creating a database of user preferences by: performing a statistical preference analysis to identify, from a collection of user-specific text instructions comprising a plurality of dental treatment instructions that are each associated with a specific user, a key preference text statement and a corresponding clinical behavior for treating a patient's teeth associated with a single user, adding, into the database of user preferences, an entry linking the key preference text statement, the single user associated with the key preference text statement, and the corresponding clinical behavior for treating the patient's teeth; receiving a description of a patient's dentition; receiving patient treatment instructions from a dental professional for performing an orthodontic procedure on the patient; and automatically generating a dental treatment plan using the database of user preferences.

A system may include: one or more processors; memory coupled to the one or more processors, the memory configured to store computer-program instructions, that, when executed by the one or more processors, perform a computer-implemented method comprising: creating a database of user preferences by: collecting user-specific text instructions comprising a plurality of dental treatment instructions that are each associated with a clinical dental procedure associated with a single user from a collection of historical treatment data; identifying, over a time period, a statistically consistent clinical behavior for treating the patient's teeth from the clinical dental procedure instructions and a corresponding key preference text statement; adding, into the database of user preferences, an entry linking the key preference text statement, the single user, and the corresponding clinical behavior for treating the patient's teeth; receiving a description of a patient's dentition; receiving patient treatment instructions from a dental professional for performing an orthodontic procedure on the patient; and automatically generating a dental treatment plan using the database of user preferences.

Any of these systems may include: one or more processors; memory coupled to the one or more processors, the memory configured to store computer-program instructions, that, when executed by the one or more processors, perform a computer-implemented method comprising: creating a database of user preferences by: collecting user-specific text instructions comprising a plurality of dental treatment instructions that are each associated with a clinical dental procedure associated with a single user from a collection of historical treatment data; identifying, over the time period, a statistically consistent clinical behavior for treating the patient's teeth from the clinical dental procedure instructions and a corresponding key preference text statement, wherein the time period comprises the duration of a most recent cluster of the clinical behavior for treating the patient's teeth; adding, into the database of user preferences, an entry linking the key preference text statement, the single user, and the corresponding clinical behavior for treating the patient's teeth; receiving a description of a patient's dentition; receiving patient treatment instructions from a dental professional for performing an orthodontic procedure on the patient; and automatically generating a dental treatment plan using the database of user preferences.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 5 is a report showing statics for a treatment plans generated automatically as described herein.

FIG. 6 is another example of a report showing details for statics for a treatment plans generated automatically as described herein.

FIG. 11 is a table illustrating examples of the results of a similarity search between different reference and found text from a user's text description, showing a percentage of similarity.

FIG. 12 is another example of a workflow for a first method of determining a collection of user or user group preferences.

FIG. 13 is table showing examples of a similarity searching done for word matching using a Damerau-Levenshtein (D-L) distance estimate.

FIG. 14 is an example illustrating the calculation of a similarity estimate using semantic similarity.

DETAILED DESCRIPTION

Figure 1:
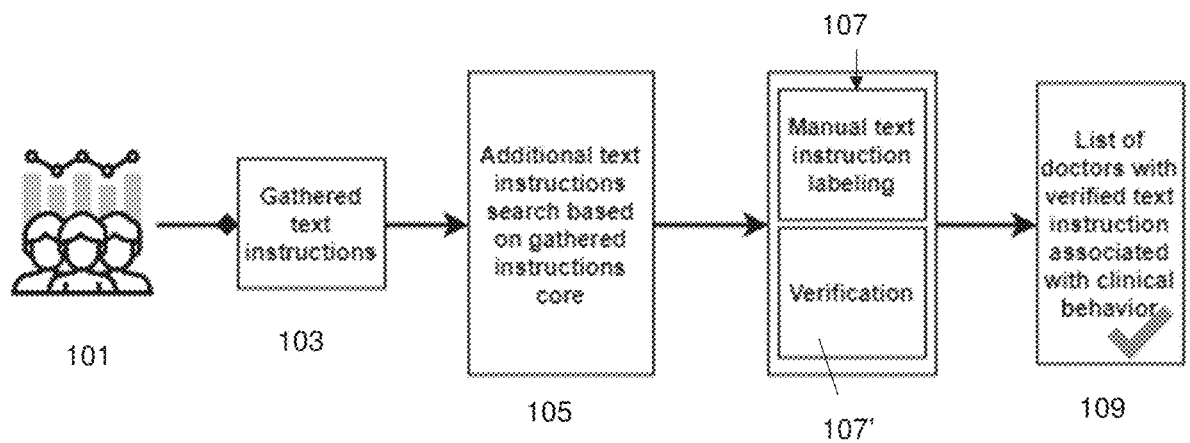
FIG. 1 illustrates a workflow for a first method of determining a collection of user or user group preferences.

Many medical professionals have strong preferences for the way in which they perform even standard medical treatments. For example, dental medical professionals (e.g., dentist, orthodontist, dental technician, etc., referred to herein as "users") may assist in the design of a treatment plan for moving or aligning a patient's teeth. As part of the treatment plan, the user may provide patient dental information (e.g., a model or scan of a patient's dental arch), along with instructions and/or preferences, and may receive a proposed treatment plan for aligning the patient's teeth. In many cases, the user may then modify the treatment plan, often by communicating with a technician, so that the treatment plan may be adjusted and again provided to the user. This process may be repeated multiple times. Although it is generally desirable to simplify this process and reduce the number of corrections or adjustments (collectively, "modifications") of the treatment plan, it is also desirable to ensure that the final treatment plan meets with the preferences and treatment goals of the user. The methods and apparatuses described herein may help ensure that the user's preferences, both explicit and implicit, are accounted for as accurately as possible in an automatically generated treatment plan.

User preferences can be defined by the user explicitly and/or interpreted based on an analysis of the user's past behavior in treating patients. The methods and apparatuses (e.g., devices and systems, including, but not limited to software, firmware and hardware) described herein may build a collection of user-specific (and/or user group) preferences, may maintain and/or update this collection of user and/or user group preferences, and may apply this collection of user and/or user group preferences in order to automatically or semi-automatically generate a treatment plan specific to a patient and customized based on user preferences. Although the methods and apparatuses described herein may be specific to a particular user (e.g., a single, specified, user), in some variations the methods and apparatuses described herein may be applied to groups of two or more users (e.g., in a practice group) or a specified user or group of users may choose to apply the preferences of another user or group of users.

The collection of user and/or user group preferences may be structured as a database, a data store, or any other appropriate data structure. The collection of user and/or user groups may therefore be referred to as a user and/or user group preferences data structure, and may be, but does not have to be, a list. The collection of user and/or user group preferences may be stored in a single location (e.g., on a remote server) or distributed in multiple locations. The collection of user and/or user group preferences may be duplicated locally and updated from one or more different sites.

The collection of user and/or user group preferences may include information including multiple users (or user groups) and associated instructions, which may be referred to as key preferences, as well as one or more associated clinical behaviors. For example, a particular physician, Dr. X, may be associated with one or more key preferences, e.g., no attachments in overcorrection, extract teeth between stages 2 and 3, etc., and each key preference may be associated with one or more (and in some cases, a single) clinical behavior that may be applied to a treatment plan, e.g., remove attachments from overcorrection, perform extractions at stage 3, etc. The clinical behavior may be standardized, e.g., into a domain-specific orthodontic treatment language (see, e.g., U.S. patent application Ser. No. 16/399,834, titled "SYSTEMS AND METHODS FOR TREATMENT USING DOMAIN-SPECIFIC TREATMENT PROTOCOLS," filed on Apr. 30, 2019, herein incorporated by reference in its entirety).

In general, methods and apparatuses for creating and/or modifying, including updating, the collection of user and/or user group preferences are described herein. The collection of user and/or user group preferences may be initially or partially based on historical data analysis from one or more users. The methods and apparatuses described herein may be specific to a single user or group of users. However, in some variations common or standard key preferences (e.g., instructions) from other users or groups of users may be used, at least initially, for some or all users. Thus, the methods and apparatuses described herein may form the collection of user and/or user group preferences, may monitor and update the collection of user and/or user group preferences, and may apply the collection of user and/or user group preferences to the automatic generation of a treatment plan.

For example, the methods and apparatuses described herein may provide for the automation of treatment planning by first identifying key preferences for a user (or group of users). This process may be automated. Identifying key preferences for a particular user or group of users is a complex process and the methods and apparatuses described herein provide variations (some or all of which may be combined in whole or in part) to build and modify the collection of user and/or user group preferences to include all or a relevant subset of key preferences for each user or group of users. Each user or group of users in the collection of user and/or user group preferences may include the same or different key preferences.

For example, in some variations a user may provide, in addition to information (e.g., dental information) about a particular patient, requests (e.g., written requests) for some key preferences, corresponding to some kind of action that the user wishes to be included or accounted for in the treatment plan. This may be included as part of a prescription form (e.g., a "Treat RX form") and may be written in free text (using user-specific language, jargon or notation). Without automation, these key preferences must be interpreted by a technician and applied to the design of the treatment plan, or across multiple treatment plans specific to that user or user group. However, users may express their key request in very different ways (e.g., "from the last aligner of active treatment, to start to remove all attachment", "end attachments after second to last active stage so the last two active stage have no attachments", "REMOVE ALL attachments AT THE 1ST passive ALIGNER", etc.). Further, users may write their instructions using different languages (e.g., English, French, Spanish, Chinese, German, Japanese, Portuguese, Turkish, Korean, etc.). For example, "remove attachments at the end of treatment" is a very common instruction used by many or all users, but may be expressed in a variety of different ways, which may negatively impact treatment processing, because if performed manually, technicians may have to take time to read, implement and re-check even such well-known and common instructions. Furthermore, in some instances, even very similarly expressed key preferences may be different between different users.

The methods and apparatuses described herein may address these concerns in a variety of ways. For example, these methods and apparatuses may build and maintain the collection of user and/or user group preferences by text mining user instructions from a collection (e.g., database) of approved treatment plans associated with the user or group of user and their instructions specific to the approved treatment plans (which may be referred to as historical treatment data). Text mining may include text matching (including, but not limited to text matching by semantic similarity) and/or machine learning as adapted specifically to key preferences. In addition to text mining, these methods and apparatuses may concurrently identify user-specific and/or generic clinical behaviors associated with each key preference identified. The associated clinical behaviors may be based on verified clinical behaviors from the approved treatment plans.

Alternatively or additionally, the collection of user and/or user group preferences may include one or more key preferences that are determined from an analysis of the user's historical treatment plans that are not explicitly expressed by the user. For example in some variations the method and/or apparatus may include a statistical analysis of the clinical behaviors from the user's treatment plans; in some variations this statistical analysis may be based on current (e.g., recent or consistent as determined analytically) user practice from user treatment plans. The method or apparatus may generate key preferences and associated them with the identified clinical behaviors.

Thus, the methods and apparatuses described herein may automatically and/or semi-automatically build and maintain the collection of user and/or user group preferences from a collection of historical treatment data. The collection of historical treatment data may be a database that is centrally curated (e.g., storing approved treatment plans associated with the user or group of users as well as any instructions from the user). In cases where there are one or more associated treatment plans associate with a particular user in the historical treatment data, the method or apparatus may, in some variations, first identify text instructions and identify one or more key preferences. The search for one or key preferences specific to a particular user (e.g., a specified user) may be guided by key preferences identified from other user's written instructions and/or treatment plans. For example, common key preferences may be determined for a population of other users; in some variations these other users may be part of a user group, or they may be related or they may be unrelated to the specified user.

The specified user's historical treatment data may then be analyzed as described herein, to identify key preferences and corresponding clinical behaviors from the historical treatment data; this information may be entered into the collection of user and/or user group preferences. As mentioned above, and described in greater detail below, in some variations, instead or in addition to identifying key preferences from the specified user's text instructions in the historical treatment data, the method or apparatus may look at the specified user's behavior (e.g., the clinical behavior from approved treatment plans) and correlate to the, e.g., common key preferences. Thus, the methods and apparatuses described herein may add or modify the collection of user and/or user group preferences based on text or user behavior.

For example, described herein are methods and apparatuses for forming the collection of user and/or user group preferences that includes the users (e.g., a list of doctors, dentists, orthodontists, etc.) and verified text instructions (key preferences) associated with one or more clinical behaviors. This is illustrated in FIG. 1. In this example, the method or apparatus may first find the user for whom it's possible to determine and apply some clinical behavior pattern. As shown in FIG. 1, the collection of user and/or user group preferences is referred to in this example as a "list of doctors with verified text instructions associated with clinical behavior" 109. This list (the collection of user and/or user group preferences) is formed in this example by an analysis of a specified user's 101 text instructions. These instructions became the core for the collection of user and/or user group preferences by finding and including variations of words and terms in the text instructions corresponding to key preferences. In this example, starting with a specified user or group of users 101, the method or apparatus may then identify and gather text instructions 103, e.g., from a database of historical treatment data. The collection of user and/or user group preferences may be iteratively expanded, e.g., by looking for new text instructions may refer to a specified key preference, forming a list of the most probable candidates from the text instructions, ranking them (e.g. as described in detail below, by one or more methods, including machine learning techniques and/or text matching, etc.). Ranking may include automatically eliminating those that are below a threshold rank or probability of likelihood as a key preference.

The process of searching for key preferences from the text instructions 103 may start from the most common and/or necessary key preference words or phrases, e.g., based on the gathered text instructions. As mentioned, initially, a population of a variety of different users may be examined to identify common or popular key preferences to form the instructions core. For example, a search of users who use in their text instruction and comments particular keywords corresponding to key preferences may be identified from the gathered text instructions (e.g., from the historical treatment data or a subset thereof). As a result, a list of instructions variations (possible key preferences) may be formed 105. Examples of different ways to gather, e.g., identify possible key preferences, and to grade/rank or otherwise distinguish between these possible key preferences are described in greater detail below. Based on results from the previous step a list identifying possible key preferences may be generated. This process may include an analysis of a doctor's treatment cases (e.g., the number of such cases), the text instructions and other metrics.

The method or apparatus may then optimally correlate the key preferences with the clinical behavior from the historical treatment data. For example, the apparatus or method may perform manual instruction labeling from the formed list of possible key preferences 107. Text labeling, including manual text labeling, may be performed accordingly to the key preferences. In some variations the text labeling may refer to the association of key preferences with a particular clinical behavior. This process may be semi-automatic (e.g., assisted or reviewed by a technician, though automatically generated). As shown in FIG. 1, the procedure may optionally include a verification step 107'. The verification may include manual review (e.g., by a technician). For example, labeled key preferences (e.g., instructions) may be validated by a responsible person with required level of clinical knowledge.

Figure 2:
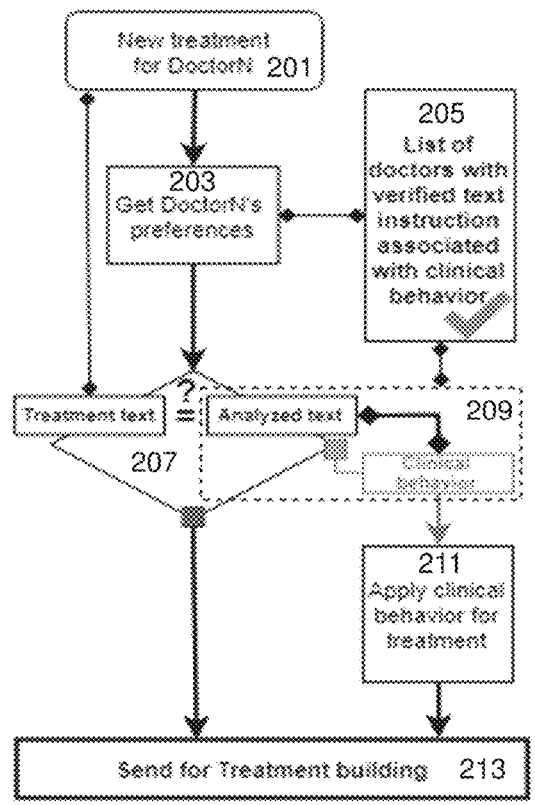
FIG. 2 illustrates a method of automatically generating a treatment plan and creating a series of dental aligners for treating a patient.

Once the collection of user or user group preferences has been constructed 109 (in this example, as a list of doctors with verified text instructions associated with clinical behaviors), it may be used to detect key preferences and apply the corresponding clinical behaviors to generate treatment plans for the user. FIG. 2 shows one illustration of a method of using the collection of user or user group preferences to automatically generate a treatment plan for a specified user that is customized to a patient. The collection of user or user group preferences (e.g., "formed list of doctors with verified text instruction associated with clinical behavior") is a key-value structure for each user, where value is clinical behavior and key is text instruction that corresponds to this behavior. In some variations, a text instruction matching process (the same process that may be used to identify key preferences when creating the collection of user or user group preferences, or a different text matching process) may compare the user's text instructions for treating the patient with the collection of user or user group preferences. When a sufficiently close match between the user's treatment text is found for the key preferences associated with the specified user or group of users, the corresponding clinical behavior may be automatically included in the new treatment plan. Thus, in some variations, only when treatment text matches a key preference is the clinical behavior applied. In general, text matching may not be case sensitive and may ignore punctuation.

For example, as shown in FIG. 2, a method of automatically generating a treatment plan is shown. In this example, it is assumed that the collection of user or user group preferences 205 has already been generated; alternatively or additionally, the method may include generating the collection of user or user group preferences, as shown schematically in FIG. 1. In FIG. 2, the apparatus (e.g., a treatment planning engine) may receive patient-specific information (such as a description of the patient's dental arch, including one or more scans, etc.) as well as treatment text from the user, comprising a request for a new treatment plan for a patient 201, in this example the user is "DoctorN". The method or apparatus may then determine the user's (DoctorN's) treatment preferences 203, which may include accessing the collection of user or user group preferences and/or generating the collection of user or user group preferences, and identifying the user, DoctorN, from the included users. Is some variations, if the specified user, DoctorN in this example, is not already part of the collection of user or user group preferences 205, then this user may be added to the collection of user or user group preferences, as described above. For example, the method or system may examine the collection of historical treatment data to identify key preferences and associated clinical behaviors, and add them to the collection of user or user group preferences. In some variations, the system may update the collection of user or user group preferences for the specified user when the specified user requests a new treatment plan (or a treatment plan for a new case).

The user's preferences, as included in the collection of user or user group preferences 205, may then be compared to the treatment text 207 by comparing the treatment text to the key preferences in the collection of user or user group preferences ("analyzed text") 209. This may include text matching and/or machine learning, as will be described in greater detail below. Where a sufficient match is identified, the corresponding clinical behavior from the collection of user or user group preferences may be automatically included in the treatment plan 211. Once all of the key preferences has been identified (and/or updated and identified), they automatically generated treatment plan may be generated and either sent for treatment building 213 or sent for review by to the user before sending for treatment building. If the user has modifications to the treatment plan, these modifications may added (as a new or updated treatment text) and automatically reviewed as described above (e.g., by analyzing the text 209).

As mentioned briefly above, any of the variations described herein the collection of user or user group preferences may be updated and/or created by reviewing the treatment text to identify key preferences. For example, in variations in which the collection of historical treatment data include a sufficient number (and/or a sufficiently recent) number of cases, which may be statistically determined, as described below, the method or apparatus may compare the text of the treatment text with the user's previous text instructions from the collection of historical treatment data to identify any user-specific key preferences. When there is a match of sufficient confidence (which may be manually or semi-manually reviewed or curated) the key preference may be added for this user or group of users to the collection of user or user group preferences.

In any of these methods and apparatuses described herein, the user may also or alternatively select a group of users from which key preferences may be selected. For example, a specified user may select (e.g., at the time of requesting the new or updated treatment plan) that they follow another user or group of users, such as a key opinion leader and/or a practice group. In some variations, the method or apparatus may then either apply the key preferences from the other use or group of users and/or may identify key preferences corresponding to those of the key preferences identified for the other user or group of users for the specified user, and apply the corresponding clinical behavior for each of those key preferences from the other user or group of users description in the collection of user or user group preferences.

Figure 3:
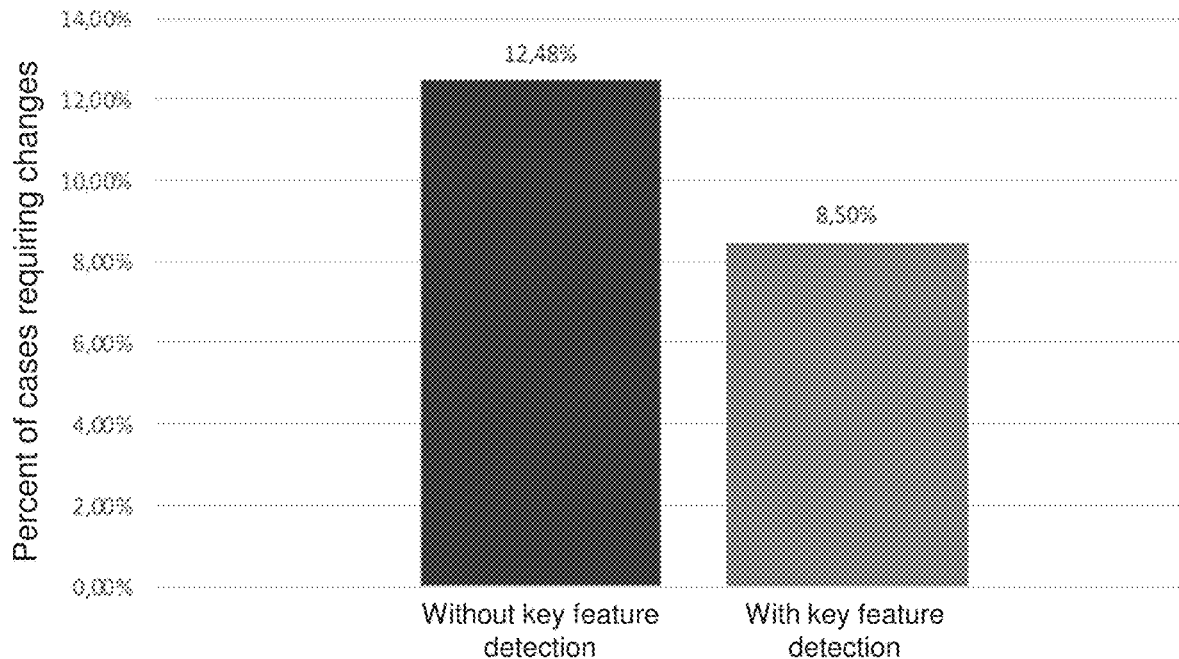
FIG. 3 is a graph illustrating an improvement in automatic treatment plan generating (showing a reduction in automatically generated treatment plans requiring modification by the user) using one variation of the methods for automatically generating a treatment plan, as described herein.

In practice, the approach described above may ensure that the application of key preferences is based on accurate text matching with pre-validated text patterns. This can be used to accurately and efficiently generate one or more treatment plans. Moreover, the treatment planning process time duration may be significantly decreased. For example, FIG. 3 illustrates an example of a graph showing the percentage of cases (treatment plans) requiring changes, which may require manual attention, to the treatment plan, based on user modifications to the treatment plan, was dramatically decreased following implementation of the approach described above, decreasing from 12.48% to 8.5%.

Monitoring

In any of the methods and apparatuses described herein the identified key preferences and/or the clinical behaviors may be checked and verified, e.g., manually or semi-automatically. This may reduce the risks of incorrect detection and errors which may prevent the user from accepting the automatically determined treatment plan(s). In addition, users may change their clinical behavior, such that previously detected key preferences may become invalid. Thus, described herein are monitoring (quality monitoring) methods and tools for performing the monitoring. These methods and/or tools may be implemented into the methods and apparatuses described herein, and may help detect cases where a user's text instructions and/or clinical behaviors (e.g., applied treatment options) differ from those of a final accepted treatment plan; e.g., differ from the intent of the user. In general, these monitoring techniques or tools may aggregate data from different treatment plan creation stages and may provide a report or metric indicating how well clinical behavior corresponds (or does not correspond) to user's text instructions.

The monitoring may be used as a quality control system and it can aid in clinical preferences detection workflow. For example, as a part of quality control system, it may provide actual information about how robust the automatic preference detection technique (and/or a method or apparatus implementing them). If the preference detection and/or clinical behavior associated with it (e.g., in the collection of user or user group preferences) is incorrect, then such cases may be further processed, and/or the collection of user or user group preferences updated or corrected.

Figure 4:
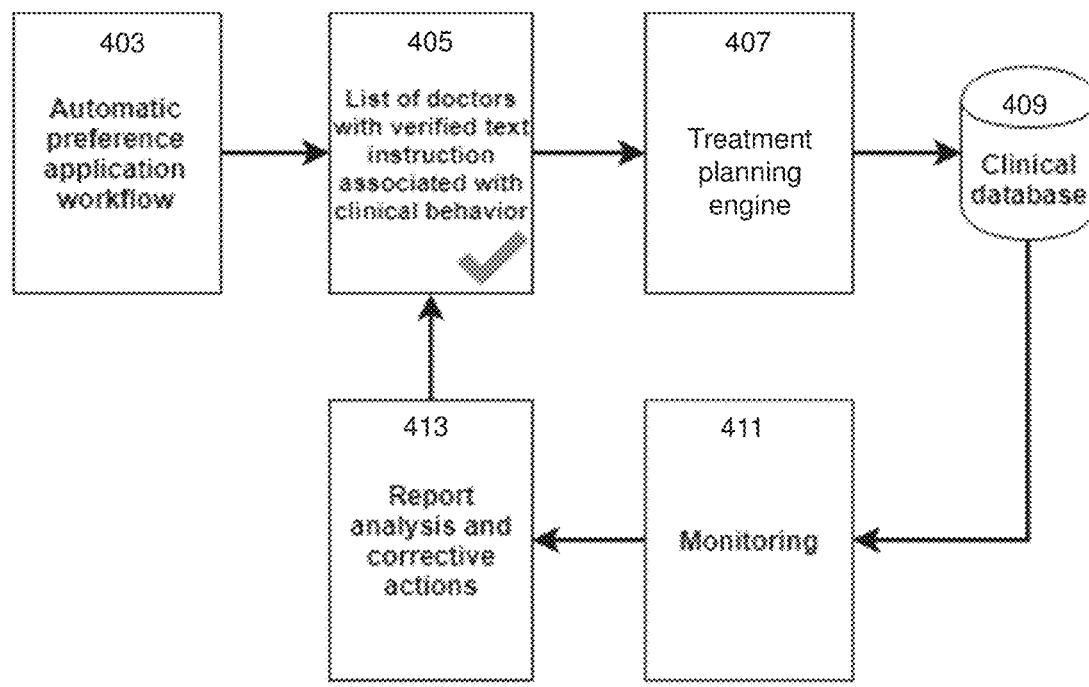
FIG. 4 is an example of a workflow (e.g., method) implementing monitoring of the collection of user or user group preferences and/or automatic generation of treatment plans using the collection of user or user group preferences as described herein.

For example, FIG. 4 shows an example of a workflow (e.g., method) implementing monitoring of the collection of user or user group preferences and/or automatic generation of treatment plans using the collection of user or user group preferences as described herein. In FIG. 4, a monitoring tool is included as a part of a clinical preferences detection workflow and may detect how and when user behavior was changed, in addition to recent behavior detection algorithms. In this exemplary method, a treatment plan (treatment plans) may be generated automatically or semi-automatically, as described above, e.g., in reference to FIGS. 1-3. These methods may also include the creation 403 and/or maintenance of a collection of user or user group preferences 405 (referred to in this example as a "list of doctors with verified text instruction associated with clinical behavior"). As described in FIG. 2, above, the collection of user or user group preferences may be used to automatically generate one or more treatment plans, when provided with, e.g., a treatment planning engine 407 receiving patient-specific information of the patient's dental arch and user instructions/requests (e.g., treatment text). Thus, the treatment planning engine may access the collection of user or user group preferences and, applying one or more techniques for text matching and/or machine learning, may identify key preferences and associated clinical behaviors and apply them to automatically generate a treatment plan. This treatment plan may then be provided to the user for verification/finalizing and, once finalized, may be added to the clinical database 409 (e.g., which may include, but is not limited to a collection of historical treatment data. The clinical database and/or treatment planning engine may also include one or more indicators of how many iterations were required before the treatment plan was finalized and accepted, and/or what corrections or requests were made by the user prior to finalizing and/or accepting the treatment plan. A monitoring tool 411 may then access the clinical database and/or the collection of user or user group preferences to review the treatment plan(s) and to analyze and provide a report 413, including corrective actions, based on the data from the clinical database. This review data may be used to improve and/or correct the collection of user or user group preferences.

For example, the collection of user or user group preference may be generated and/or modified as a result of the automatic preference application workflow, and my provide information about whether specific treatment options should be automatically applied to current case. During the process of treatment plan creation, the clinical database may collect statistics, including but not limited to data about all treatment options which were applied or not applied. The monitoring may use this data to provide a report for specified period how well the automatic preference application, e.g., for example, how well the text matching works when comparing the collection of user or user group preferences to the user's instructions and/or how complete or correct the collection of user or user group preferences is. For example, a report from the monitoring tool may include any one or more of: (1) the overall number of initially submitted cases; (2) the number of initial cases with recognized text instructions and corresponding treatment options that were automatically applied; (3) the number of accepted cases where automatically applied treatment options were remained; (4) the number of accepted cases where automatically applied treatment options were changed for some reason; (5) the number of accepted cases without automatically applied treatment options where such options were applied manually during treatment plan creation; (6) and the number of accepted cases without automatically applied treatment options where such options were not applied manually. The reports may also include or indicate the user(s) corresponding to any cases that were modified.

This data can be generated either generally for all users or for each particular user. Data from items (1) and (2) may be used to evaluate an impact of automatic preference application workflow on treatment planning. For example if the text instructions were changed or the user's clinical behavior was changed (e.g., the user does not use a corresponding feature anymore).

The data from items (3) to (6) may provide a good/bad detection ratio. Cases from items (3) and (6) may follow positive scenarios: it is excepted that treatment option may be applied if a text instruction exists and won't be applied if there is no such text instruction. Cases from item (4) may follow a negative scenario: a detected preference doesn't fit to the user's actual needs. This may be investigated in detail and it may be possible that this text instruction may be excluded from the list. Cases from item (5) may be marked as neutral; there may be many circumstances when applied treatment options are case-specific and a user did not specify this in text. However, if a user has a lot of such cases, this may indicate that the system may flag this user to be aware of such exceptions.

The monitoring tool described herein may provide different kinds of reports, including reports to the user and/or feedback to the treatment planning engine. An example of brief report with statistics for multiple users is shown below in table 1 (FIG. 5). In some variations a more detailed report with statistics for each user may be generated, an example of such a report is shown in table 2 (FIG. 6). Positive cases were approved, negative cases indicated cases that were not approved (and may convert to positive cases with correction). For example, if a user has a relatively large negative cases ratio (or percent of negative cases), then either the user or the administer (operating the treatment planning engine, for example) may the user's cases to find the reason why and determine whether either the key preference should be excluded and/or the associated clinical behavior should be modified and/or excluded. In some variations, low positive cases numbers (e.g., percent of positive cases) along with a high neutral cases ratio (e.g., a percent of neutral cases) may indicate that the user's behavior was changed and all or some of the key preferences are outdated and should be updated or removed.

Text Searching

The methods and apparatuses described herein may identify key preferences from user text instructions (e.g., treatment text instructions) based on matching of the treatment text instructions with known text patterns corresponding to the key preferences and/or clinical behaviors. Generally referred to as text searching or text matching, described herein are a variety of techniques that may be adapted for use to identify key preferences during one or more of: creating the initial collection of user or user group preferences for one or more user or groups of users by reviewing a collection of historical treatment data and comparing the historical text instructions of the specified user against a known key preference(s) or comparing historical text instructions of the specified user against other historical text instructions of the specified user; and/or comparing the current text instructions of the specified user against key preferences already in the collection of user or user group preferences, etc. Thus, the text searching, which may also be referred to herein as and may include text matching, may be adapted for use in any of the methods and apparatuses in which user text is being compared to other text in order to identify and/or score the match between portions of text, such as key preference text and/or clinical behavior text. The text searching/text matching techniques described herein are adapted specifically to expand text patterns and may provide a confidence score that may be used to indicate a positive or negative match.

In some variations the techniques for text matching described herein may include one or more machine learning techniques adapted for use. For example, described herein are machine learning techniques for finding a match (or for scoring a match) between a user's text instructions and one or more key preferences. In general one or more text matching techniques adapted for matching identified or putative key preference text with user text may incorporated into any of the apparatuses and methods (e.g., into the workflows) described herein. For example the machine learning technique for text matching to identified or putative key preferences may be integrated into existing workflow as shown schematically in FIG. 7.

Figures 7, 8:
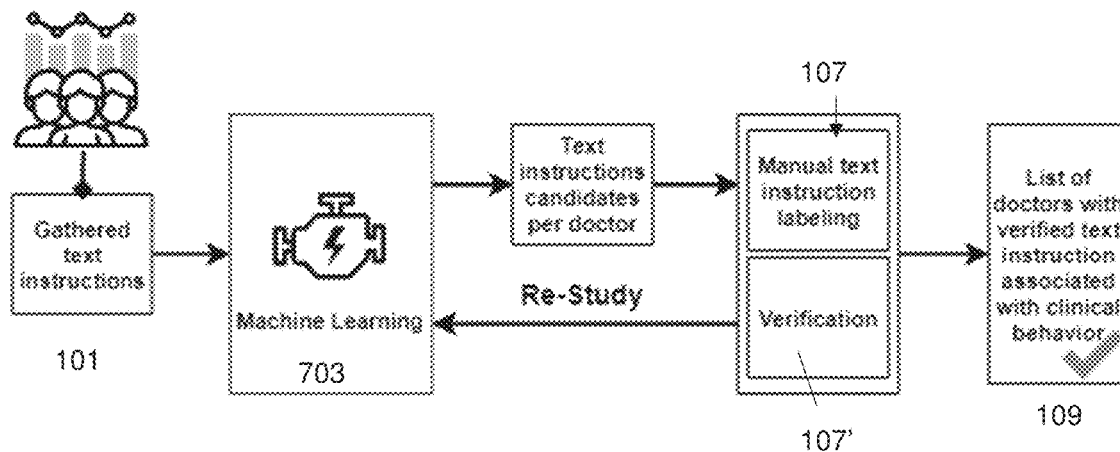
FIG. 7 is another example of a workflow for a first method of determining a collection of user or user group preferences.
FIG. 8 is a table illustrating instructions from different users ("preference text") that the machine learning agent has classified into either positive or negative categories.

FIG. 7 is similar to the workflow (e.g., method) shown in FIG. 1, but includes the use of machine learning 702 as part of the gathering 103 and searching 105 of text instructions. In this example, the collection of user or user group preferences is both crated by the use of a machine learning text matching technique and identification of key preferences in the user's text instructions and key preferences from the collection of user or user group preferences may be accomplished by a machine learning technique. For example, in some variations, a text matching engine may be configured as a machine learning agent (e.g., engine) that is trained on key preferences identified from the collection of historical treatment data for each clinical behavior. Further, trained models may analyse the user's text instructions within the historical treatment data for a specified period of time period extending from the most current time period to a period determined to remain accurate, as determined by a statistical analysis such as described below (e.g., indicating a consistent user of the same key preferences and/or clinical behavior(s)). The result may be a list of text instructions (putative key preferences) that have a high probability of corresponding to the target clinical preference. The identified putative key preferences may be reviewed (e.g., curated) by a technician or other person with sufficient clinical knowledge; thus, the putative clinical behavior may (at least initially, when training the engine) be manually labeled after verifying each identified putative key preferences and/or clinical behavior. The resulting verified key preferences may be keep as a the final key preference list associated with a clinical behavior and these instructions may be used to expand training and test datasets for further machine learning of key preferences.

For example, a machine learning (ML) engine may identify at an example of a key preference such a "extract teeth on defined treatment stage" from a user text instruction, e.g., a set of gathered text instructions. These text instructions may be split onto two datasets for ML purposes: instructions which express a user's desire to perform teeth extraction at a particular treatment stage (e.g., a positive dataset), and any text instructions which is not related to this preference type (e.g., a negative dataset). Text instructions examples that may be considered part of a positive dataset may include, for example: "Extractions Ext at Stage 2", "Extractions will be done after aligners placed following tray 1", "aligner Extractions from 2", and "Delay Extractions until second aligner". Text instructions that may be part of a negative data set may include, for example: "No Extractions", "Extractions of the 4s when young", and "trim extra 1 mm all aligners both buccal and lingual".

Trained ML classification models may then be used to analyze the user's text instructions related to recent treatments. For each text instruction, the machine learning agent may classify the text instruction as belonging to one of the two classes (positive or negative). As a result, a dataset (e.g., list) of the user's text instructions may include a classification for each text instruction classifying it into either positive or negative. The resulting classified dataset may be marked and verified. The table (table 3) in FIG. 8 illustrates an example of text instructions from different users ("preference text") that the machine learning agent has classified into either positive or negative categories.

The machine learning agent may be modified to improve the classification of user text information as either matching (positive) a particular key preference, or not matching (negative) the particular key preference. For example, to achieve better classification, one or more filters may be applied to the user text instructions being analyzed, for both training and application to the instruction text from the specified user. For example, the text may be first transformed to all lowercase (or uppercase) text; the text may be filtered to ignore or remove certain character is or symbols, such as digits, punctuation, common words (e.g., Hi, thank you, bye. etc.); the text may be split into short phrases (e.g., by line ending, by sentence ending, by punctuation, etc.).

In general, any appropriate machine learning model may be used for text classification, including but not limited to: random forest, bag of words, and weod2vec. For example, random forests or random decision forests are an ensemble learning method for classification, regression and other tasks that operates by constructing a multitude of decision trees at training time and outputting the class that is the mode of the classes (classification) or mean prediction (regression) of the individual trees. Random decision forests correct for decision trees' habit of overfitting to their training set.

The bag-of-words model is a simplifying representation used in natural language processing and information retrieval (IR). In this model, a text (such as a sentence or a document) is represented as the bag (multiset) of its words, disregarding grammar and even word order but keeping multiplicity. The bag-of-words model is commonly used in methods of document classification where the (frequency of) occurrence of each word is used as a feature for training a classifier.

Word2vec may refer to a group of related models that are used to produce word embeddings. These models are shallow, two-layer neural networks that are trained to reconstruct linguistic contexts of words. Word2vec takes as its input a large corpus of text and produces a vector space, typically of several hundred dimensions, with each unique word in the corpus being assigned a corresponding vector in the space. Word vectors are positioned in the vector space such that words that share common contexts in the corpus are located in close proximity to one another in the space.

The ML agent described herein may simplify and increase the speed of searching new text instructions without additional cost, and may provide significant improvements in text matching using a ML agent.

Figures 9, 10A, 10B:
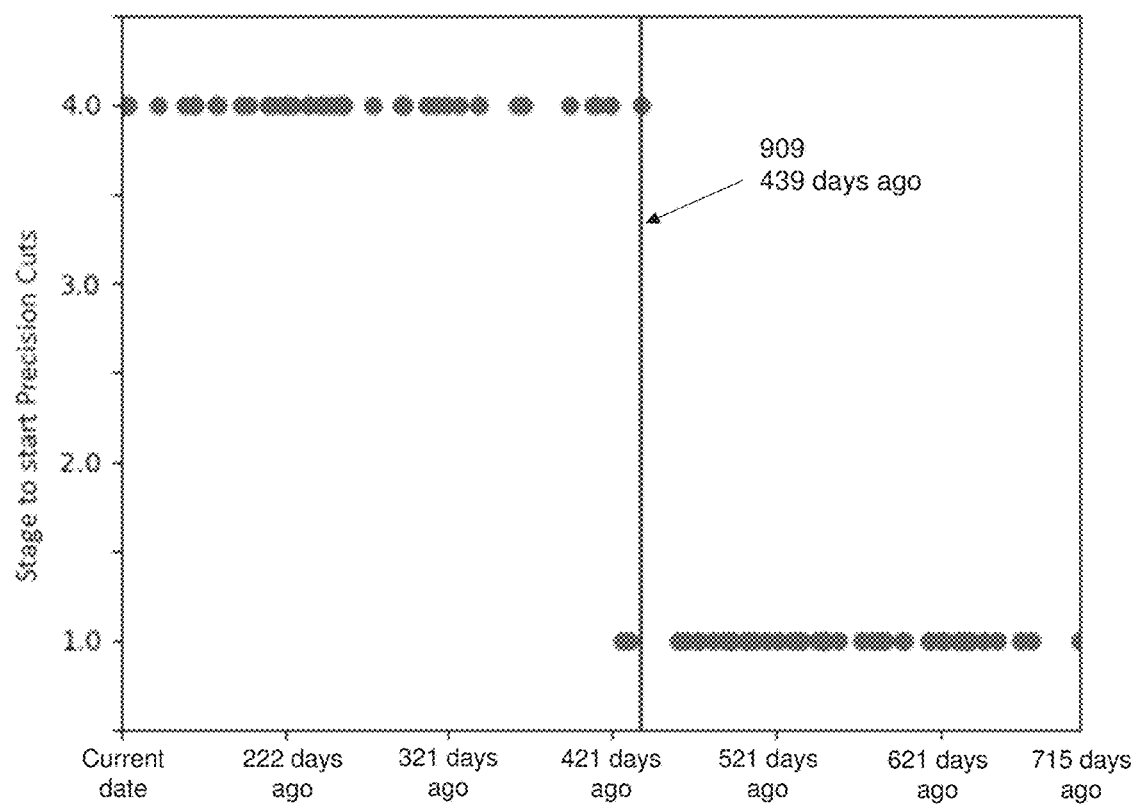
FIG. 9 is a graph showing an example of an analysis of a key preference term as used by a user over time.
FIG. 10A is an example of three text instructions that are marked by different values (shown as text units or words with numerical values above them) using a machine learning technique for text matching between phrases of words.
FIG. 10B illustrates the probability of a match between each of three statements and a target statement (e.g., a key preference statement of "Start Precision cuts at the stage #").

Returning to FIG. 7, the ML agent 703 may be included in the workflow as at least part of a text classification system that may be used to automatically generate a list of candidate key preferences from the user's text instructions 101. For example, in some variations the ML agent may be configured to use a modified Bag of Words model to train and find key preferences from user recommendation text. As mentioned, candidate key preferences identified (putative key preferences) may be manually or semi-automatically reviewed or assessed to confirm that the identified terms from the text instructions are related to the key preference(s). The classification model may be improved by using, for example, convolutional neural network (CNN) for the text classification problem. In some variations the ML agent may be required to work with an absence of data sets for training and testing, and thus data labeling may be performed only after text classification has already been done. For each new key preference that may be text matched in order to aid in automating the generation of the treatment plan, only a small set of (in some cases manually gathered) text instructions may be used. Thus, in instances where the data set is very small, is not balanced and is "dirty", a trained model may typically have a very low efficiency. This may be addressed by using a clinical analysis technique that provides the most regular recent clinical behavior and individual data for each user, corresponding to actual user (or group of users) data, e.g., configured treatment plans and instruction sets that are recent within a defined or determined time period having a high confidence level. For example, FIG. 9 shows an analysis of the key preference term "Start Precision Cuts at the stage #" for a particular user from the collection of historical treatment data that includes treatment plans and user instructions for a large number of users collected over two years (FIG. 9 shows a time period extending from a first date 715 days ago to a second date, e.g., the current date). The vertical line 909 in FIG. 9 indicates a date (439 days ago) after which the user has shown a clear clinical pattern. Precision cut stages for recent cases are shown on the left from the vertical line and older cases are shown on the right. Thus, the ML agent may more effectively consider all the user's text preferences only since the current treatment preference has been established, e.g., from 439 days ago, as positive samples. Thus, by restricting the data to only the current clinical behavior corresponding to the key preferences, the ML agent may be trained and may operate more reliably to determine the positive class, while the negative data set can be formed by the user's preferences that do not have any behavior pattern (mess of stages). This approach may be useful to classify whole user's text, which may include a number of different text instructions (usually equal to at least one sentence). However, it may be more helpful to determine which short instructions correspond to the user's intention related to the putative key preference (target). Thus, the ML agent may use a Bag of Words ML model that matches some words with values corresponding to their significance at the text's class calculation process. As an example, FIG. 10A illustrates an example of text instructions that are marked by different values (shown as text units or words with numerical values above them). The greater numerical values may correspond to greater significance of the word for the class of text, where the user instructions request a target preference such as "Start Precision Cuts at the stage #". For simplicity, these values may be referred to as conditional probabilities of whole text that corresponds to a target class if it contains the word. In the following description these conditional probabilities may be marked as:

$$P(\text{class}^+|\text{word})$$

The probability of a sentence expresses user's target preference can be calculated as the following sum:

$$P(\text{sentence} \in \text{class}^+) = \sum_{i=1}^{N} P(\text{class}^+|\text{word}_i) \times I(\text{word}_i \in \text{sentence})$$

Where:

$P(class^+|word_i)$ is a conditional probability that a user's whole text has instructions related to target preference, if it contains word with i-th number. N is a total number of unique words in the whole data set.

$I(word_i \in sentence)$

I is the indicator function displaying that sentence contains i-th word. The same probability can be found by a Bag of Words model on the whole instruction/sentences basis instead single words, as shown in FIG. 10B.

Thus, from this approach conditional probability for each unique instruction at the data set can be calculated:

$P(class^+|instruction_j)$ where j<M is the total number of unique instructions.

To be able to calculate probability for arbitrary sentence based on included words, the following model may be fit:

$$\sum_{j=1}^{M}\left(\sum_{i=1}^{N}\alpha_i \times P(class^+ | word_i) \times I_j(word_i \in instruction_j) - P(class^+ | instruction_j)\right)^z \rightarrow \min$$

As a result, the probability for arbitrary sentence may be assessed as:

$$P(sentence \in class^+) = \sum_{i=1}^{N}\alpha_i \times P(class^+ | word_i) \times I(word_i \in sentence)$$

These estimated probabilities may then be used to determine, based on this ML agent using bag of words, if the examined text includes the key preference.

Alternatively or additionally, text searching may include one or more text matching techniques that perform a similarity search, such as Damerau-Levenshtein distance measures, in order to find a match between terms in a user's text instructions and one or more key preferences. As mentioned, text instruction matching with known key preferences (e.g., key preferences corresponding to clinical behavior) may apply known text pattern techniques. In some variations of the methods and apparatuses described herein, text similarity may be used to search algorithms based, e.g., on Damerau-Levenshtein distance measure to find a user's or a group of users' text instruction(s) corresponding to a key (e.g., clinical) preferences. Similarity search algorithm based on Damerau-Levenshtein distance (D-L or Edit distance) measure may find sentences in input text that are similar to a given references. For example, a similarity threshold may be specified from between 0 to 100%, 100% means that the technique should match exactly the same sentences (in this example, ignoring letters case and words order) and 0% means that completely different sentences will be matched as similar. In general, the higher threshold may provide more accurate results and lower thresholds may give more positive matches but may also significantly raise the error rate (false matches).

FIG. 11 is a table showing examples of text similarities using reference key preferences when applying a similarly search, e.g., an edit distance (e.g., a D-L distance) measure, as all or part of the text matching/text searching. The use of edit distance may increase the number of identified key preferences, particularly when used in addition to a Machine Learning (ML) approach such as one of those described above, up to 20%. In addition, an edit distance measure may also significantly reduce the amount of time to create the initial dataset and text samples in comparison with manual text labeling. This improvement is even greater when the labeled text language isn't native for person who performs labeling.

FIG. 12 is another example of a schematic of a workflow (e.g., similar to FIG. 1 and FIG. 7) that includes the use of an edit distance measure as part of the text matching portion 1205 that includes both a machine learning (ML) agent 1202 and a similarity search 1204. As discussed above, there are at least two types of workflows that may include the identification of key preferences. The first type of workflow may include identifying key preferences to initially build a collection of user or user group preferences, which may include training and testing text samples that may be used for a Machine Learning (ML) agent. The trained agent may be used to analyse a user's text instructions for a long period of time. The result may be a list of text instructions (putative key terms) that have a high probability of corresponding to the clinical preference (reflecting the actual key preference). A technician with the appropriate clinical knowledges may then manually or semi-automatically label and/or verify the found instruction text as a key preference. The resulting key preferences, user identification and corresponding clinical behaviors may form the collection of user or user group preferences that can be used as an initial dataset for a similarity search technique (e.g., D-L distance measure) to expand or refine the list of found instructions. A similarity search technique may help to find text instructions that may otherwise be skipped over by ML techniques because of mistypes in key words, different word orders and in case of algorithmic inaccuracy.

In addition, a similarity search technique can be effectively used with a small amount of initial text instructions. For example, similarity searching can be used as a workflow separately from ML (e.g., without a ML agent) when the number of initial text instructions is not sufficient to train a ML agent. This may be very helpful to identify key preferences for users who write their instructions in different languages or combinations of languages (e.g. Spanish, French, Japanese, etc.). Other parts of the workflow shown in FIG. 12 may be the same as for FIGS. 1 and 7, described above. Found instructions are also must be verified by human before they will be added to the list of associated with clinical preferences text instructions. The list can be used again as initial dataset for search algorithms as long as the search gives new results.

The similarity search technique described above is a D-L distance measure that may be adapted for use with for individual words. As mentioned above, the text examined by the similarity search may first be prepared, which may increase search accuracy. For example, in some variations, the input text may be split by sentence endings (dots) or by line endings (\n); all of the digits may be replaced with placeholders; Text may be normalized by case (e.g., all lower case or upper case); and all special symbols and punctuation may be removed.

Thus, the similarity search (e.g., D-L distance determination) techniques described herein may use a word-by-word distance measure rather than or in addition to measuring a distance directly between whole sentences. If the word similarity is more then specified by a threshold then they counted as matched. Overall sentence similarity can be calculated using following formula:

$$\text{Similarity} = (\Sigma_1^n L\text{sim}_i - \Sigma_1^k L\text{diff}_j)/\text{Lall}$$

where $L\text{sim}_i$ is a length of the i-th word that is marked as similar, $L\text{diff}_i$ is the length of i-th word marked as different, Lall is the sum of all words length. If resulting similarity is more than a threshold amount, then a term (e.g., or group of terms, e.g., a sentence) will be added to verification list. FIG. 14 illustrates an example of semantic similarity in which the key preference "no attachment in overcorrection aligners" is compared to the user's instruction text, reading "Remove attachments at overcorrection". The changes necessary to make these two statements identical is shown below (e.g., 3 substitutions, 9 insertions, 4 deletions, 1 transposition), from which a similarity score can be estimated, as shown.

Thus, the D-L distance is a string metric for measuring the edit distance between two sequences. Informally, the Damerau-Levenshtein distance between two words is the minimum number of operations (consisting of insertions, deletions or substitutions of a single character, or transposition of two adjacent characters) required to change one word into the other. Using this technique, the similarity between search results may be determined. FIG. 13 shows a table (table 4) that demonstrates the word matching using the D-L distance. unique user identification, matched text from his text instruction with reference, and clinical behavior for current instruction. A technician (or in some cases the user) may accept or decline shown a suggestion. The text matching described herein may be improved by applying as a word-by-word similarity search. Thus each word from the user text instructions may be matched with each word from the reference (e.g., a putative key preference). In addition, the similarity searching may limit the size (e.g., character length or size length) of the reference key preferences to less than a match threshold, such as limiting similarly searching to compare between segments of text instructions (e.g., single sentences, phrases, etc.) that are within about 50% to about 165% (e.g., between 35%-185%, between 40%-180%, between 45%-170%, between 50%-165%, between 55% to 160%, etc.) of the length of the reference (e.g., of the putative key preference).

Figure 15:
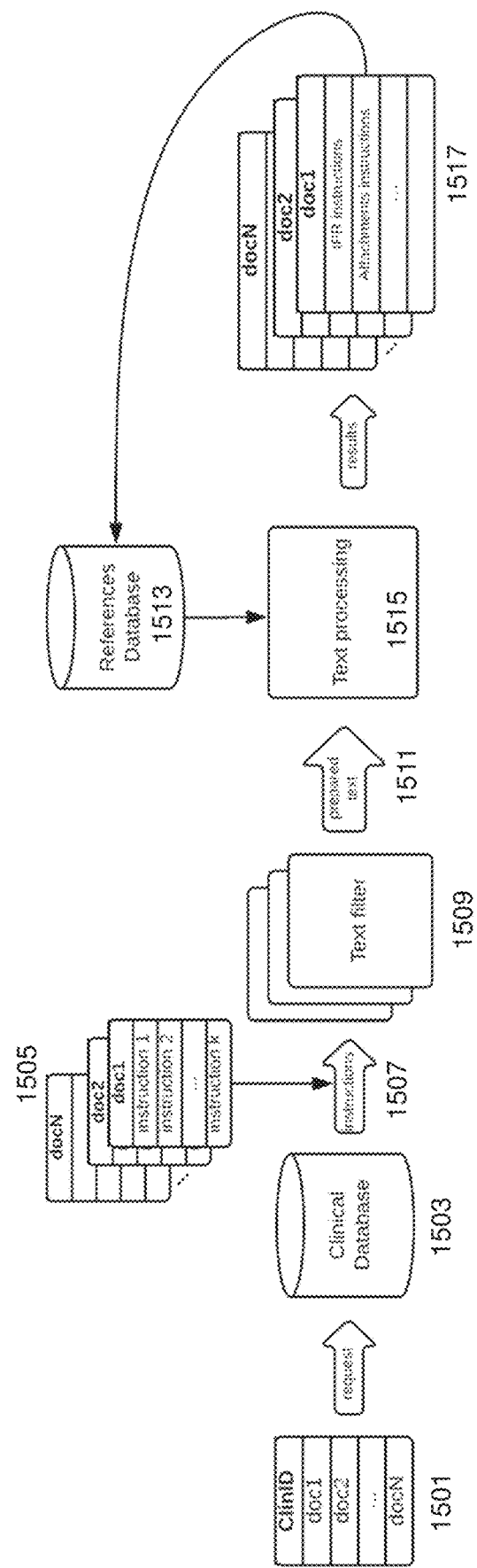
FIG. 15 illustrates an example of implementing a similarity search technique such as D-L distance.

FIG. 15 illustrates one example of an approach for implementing a similarity search technique such as D-L distance. A shown in FIG. 12, the technique may be integrated into the workflow (e.g., the method of automatically generating a treatment plan). In FIG. 15, the collection of user or user group preferences is constructed using similarity searching. In this example, the apparatus or method may get all instructions 1507 for each user 1501 (e.g., each ClinID) from a clinical database 1503, to generate data showing the instructions linked to each user 1505. The method or apparatus may then apply text filters 1509 to format the text of the instructions (e.g., all lower or upper case, removing punctuation, etc.). The prepared text 1511 may then be processed to preform the similarity search 1515 as described above, comparing the putative key preferences of each user to all or a portion the final instructions and/or clinical behavior from a collection of historical treatment data (e.g., reference database) 1513 as described above, e.g., using a similarity search technique such as the D-L distance. Results having the highest similarity that is above a similarity threshold or prediction levels (e.g., match of >X %, where X is 40, 45, 50, 55, 60, 65, 70, 75, 80, 85, 90, etc.) may be considered a true match and may be added to the collection of user or user group preferences 1517. This search may be repeated with new references to build and/or update the collection of user or user group preferences.

In general, the machine learning agent for recognizing key preference language and/or a similarity search agent may be used in generating the collection of user or user group preferences, as described above, and illustrated in the workflows of FIGS. 7 and 12. Thus, these agents (which may be referred to herein as engines) may be used separately, or together. In particular, the similarity search agent may be used to improve the behavior of the machine learning agent, for example, by expanding the positive (or negative) sets used to train the machine learning agent. Either or both of the machine learning agent (or a new machine learning agent) and the similarity search agent may be used to identify or confirm a match between the user's current text instructions and one of the key preferences in the collection of user or user group preferences. Different (and in some cases more stringent) thresholds for confirming a match may be applied for confirming a match between the user's text instructions for a new case and the collection of user or user group preferences, since the user is being compared to their own language. Alternatively, in some variations the text may have to match exactly or nearly exactly.

Statistical Preference Analysis

In some cases, the collection of user or user group preferences may be generated, expanded and/or updated by using a statistical analysis to identify users having consistent clinical behaviors and/or text instructions, even when these text instructions do not match to candidate key preferences.

Figure 16A:
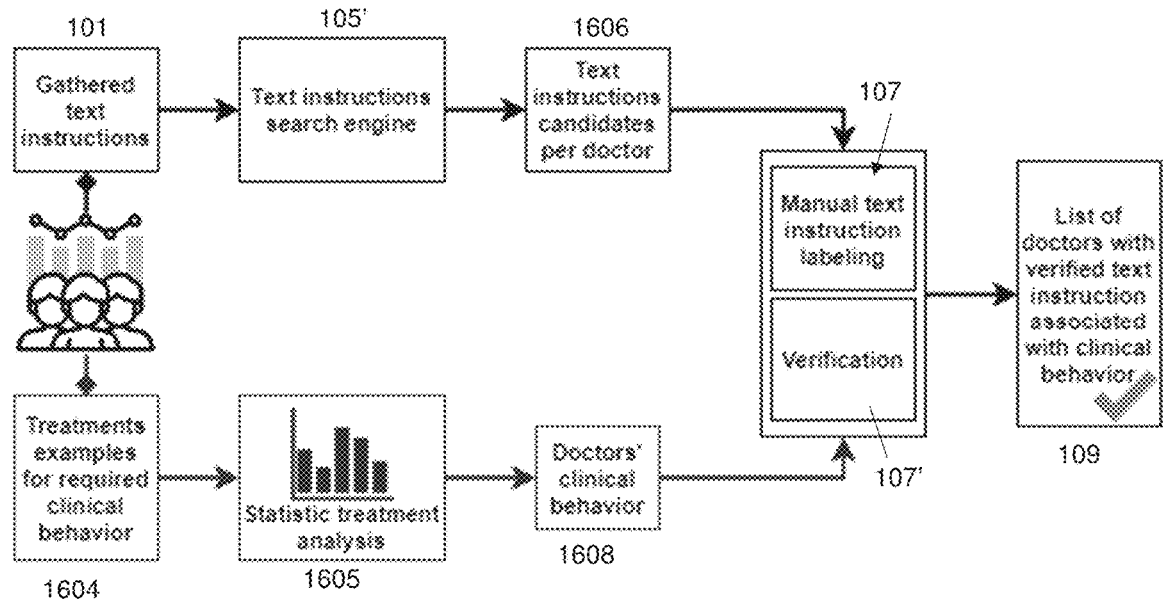
FIG. 16A is another example of a workflow for a first method of determining a collection of user or user group preferences.
Figure 16B:
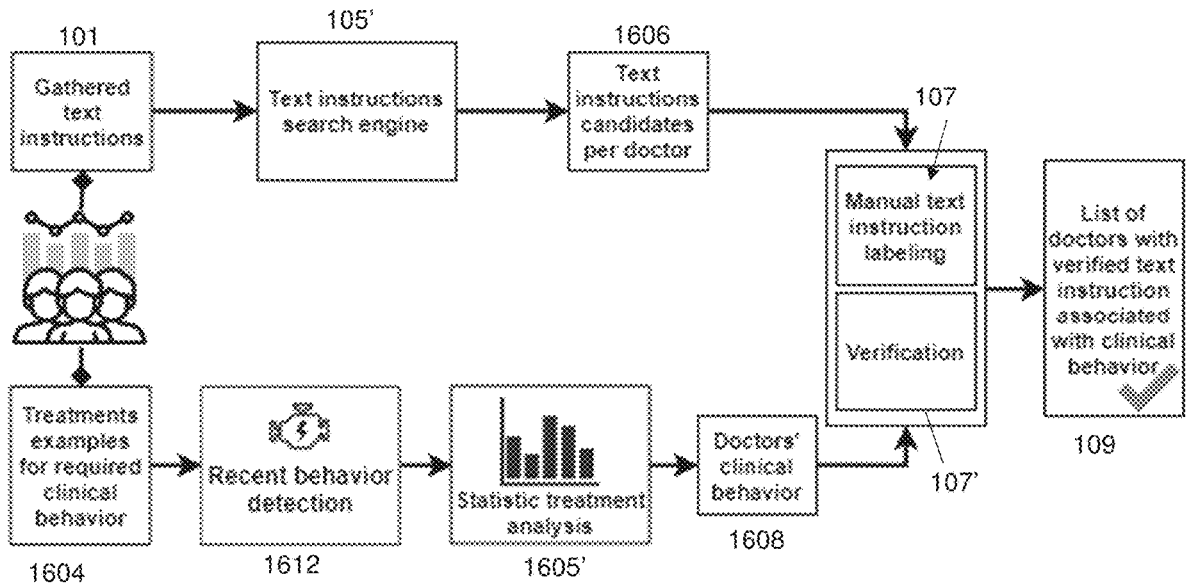
FIG. 16B is another example of a workflow for a first method of determining a collection of user or user group preferences.

Thus, in some variations, alternatively or in addition to searching user textual instructions to automatically or semi-automatically identify intended clinical instructions for generating one or more treatment plans as described above, user behavior may be used to identify clinical behavior and corresponding instructions (key preferences). For example user-specific key preferences (correlating to clinical behaviors) may be that automatically or semi-automatically determined by detecting statistically consistent clinical behaviors from the user's past behavior. In general, the apparatuses and methods, including a statistical preference analysis agent (or statistical preference analysis engine) may identify a user-specific clinical behavior and a corresponding key preference (e.g., text instructions) by examining a specified user's stored treatment data over time from a collection of historical treatment data. When, for a specified user, there is a statistically consistent behavior (e.g., treatment instruction and/or clinical behavior), the user, the user's key preference and the corresponding clinical behavior may also be added to the collection of user or user group preferences. As shown in FIG. 16A, this process may be performed in parallel with the text matching processes discussed above.

This use of a statistical analysis (e.g., the use of a statistical preference analysis agent) may improve the accuracy of the automatic interpretation of user instructions and may expand the number of users for whom automatic interpretation can be applied. These methods and apparatuses may also identify key preferences for users that do not explicitly provide text instructions for their treatments, or that do not provide them in a standard manner. These methods may therefore improve and expand the operation of the machine learning agent and/or similarity search agent. Finally, these methods and apparatuses may also or alternatively be applied to users with non-English text instructions and internal technician's protocols, and may validate previously identified user text instructions and associated clinical behaviors.

For example, a statistical preference analysis agent may determine if a specified user is highly consistent across multiple cases in the user's textual instructions accompanying a request for forming a treatment plan for a patient. The method or apparatus may set a threshold (or more than one threshold) but may otherwise look for instructions or requests that are essentially the same across multiple cases, above some threshold for comparison.

Typically, there may be common clinical behavior patterns during all user's treatment plans, which are related to different treatment phases. The most frequent clinical behaviour patterns, which may be all or a subset of key preferences (e.g., text instructions) within a collection of user or user group preferences, may be used as a starting place for performing a statistical analysis. For example, a collection of user or user group preferences may include the output of the machine learning agent and/or similarity search agent output, identifying users, corresponding key preferences for that user and clinical behaviors. A collection of historical treatment data may be analyzed for each user separately (e.g., a list of users, including users for whom the machine learning agent and/or similarity search agent did not identify any or many key preferences), to determine each user's individual behavior detection purpose.

In one variation, previously accepted user treatment plans for a specific user are investigated to identify consistent clinitial behaviour patterns. One or more metrics, such as the frequency of a treatment option appearance, and its standard deviation are calculated. This analysis may provide a metric's thresholds indicating partial clinitial behaviour. User's with stable clinical behavior pattern(s) may be assumed as candidates for further common text preferences analysis. This approach may provide an inexpensive way to generate or expand a collection of user or user group preferences, particularly when the user is using irregular key preferences (keywords), to indicate the user's clinical preference(s).

Actual (or recent) user clinical behavior detection may therefore be an additional step of or before statistical analysis. This step may assume a date after which the user has specified a clinical preference. From this assumed date until now, the users clinical behavior may therefore appear consistent. Statistical treatment analysis may be able to efficient detect this clinical behavior investigation.

A straightforward application of this technique (or implementation of a statistical preference analysis agent) may look at the statistical appearance of a particular key preference in the user's text instructions and any corresponding clinical behavior; alternatively or additionally, the method and/or statistical preference analysis agent may examine the statistical appearance of one or more clinical behaviors, including those clinical behaviors corresponding to key preferences already identified for other users in the collection of user or user group preferences. If there is very low variation for a particular user-specific key preference and/or clinical behavior (e.g., a clinical behavior common to other users and in the collection of user or user group preferences), such that the standard of deviation of an average value of a behavior is at or above a threshold value (e.g., within Y % of the average value, where Y is 5, 10, 15, 20, 25, 30, 35, 40, 50, 60, etc.).

Thus, as shown in FIG. 16A, a statistical preference analysis (or a statistical preference analysis agent) may be included in the workflow for generating a collection of user or user group preferences 109. FIG. 16A is a modification of the workflow for generating a collection of user or user group preferences shown in FIGS. 1, 7 and 12. In FIG. 16A, the statistical treatment analysis may be performed in parallel with the use of text matching (text searching 105') of gathered text instructions 101, as described above, including identifying and vetting candidate key preferences 1606 for some users, and manually or semi-automatically curating the results 107 that are then added to the collection of user or user group preferences 109. Statistical preference analysis may be performed by identifying one or more clinical behaviors of treatment 1604 and/or user-specific key preferences, and determining how consistently they are used by the user based on the historical treatment data (clinical behavior 1608). Consistently applied clinical behaviors and their corresponding user-specific key preference language (as in the parallel text matching path) are then added with the user identification to the collection of user or user group preferences after manually or semi-automatically verifying 107, 107'.

In some cases, and in particular for historical treatment data that extends over a long time period, the user may change their practice one or more time, e.g., from a first consistent practice to a second consistent practice. This may be accounted for by examining the clustering of behaviors that can be expressed numerically (e.g., for behaviors that correlate to actions taken at a particular stage of treatment, the treatment stage may be changed).

For example, in a data set of historical treatment data extending over a 1.6 year period, it may be assumed, that users can change their clinical preferences periodically at least a few times since the start of the period. Moreover, user can have more than one clinical behavior for each clinical feature at the same time, e.g. perform I PRs or Teeth extraction at various stages accordingly patient's age or product type. In general, conditions can be very complicated and it could be hard to find its clear definition. In such cases, digital preferences (like stage to perform any clinical feature, IPRs, extractions) may not have small deviation value, on which raw statistics' investigation was based.

In such cases, it may be helpful to define a date since which the user's recent individual behavior was the most strong (e.g., most consistent), and/or identify one or more behavior patterns that cover all or almost all of the user's treatment cases.

Some clinical features may be referred to as digital features, as they may be readily quantified. For example, digital features may include stage to start IPR (stage number), remove Attachments stage (stage number), etc. Non-digital features, for which it may be difficult to define distance metric, may include e.g. text instructions from comments.

Digital features may be processed in multiple dimensions (e.g., providing multiple clusters). For example, using a distance metric. A distance metric for digital features may use a Euclidean norm. For clusterization purposes the [feature]×[timeline] plane may be considered. A two dimensional (2D) distribution Gaussian Mixture clusterization model may be applied. It may be assumed that users cannot change their behavior more than some maximum number within a defined time period (e.g., no more than 5 times within 1.5 years). The models may be fitted for the various clusters, where each cluster may be considered as a user's consistent preference. So, as a result, there may be, e.g., 5 configurations with various number of clusters. One configuration may be chosen, based on the minimal mean value of standard deviations within each cluster in this configuration.

A most recent user's preference may be selected as one cluster from the selected configuration. Based on clusterization results for selected configuration, for each cluster the most early case may be found as a cluster's "since_date" property, and a cluster having the most close (to today) "since_date" may be selected. The "since_date" for a chosen cluster may be considered as last clinical preference change date. All cases since this date should be considered as including the actual, current user's preference. Thus, for all of these cases a next clusterization model may be applied. The cases from the most recent "since_date" may be processed by a KMeans clusterization model. It may be assumed that the user cannot have more than four various behavior patterns at the same time and the same preference, so a KMeans model may be trained 3 times and the best number of clusters chosen, based on overall/mean standard deviation value. Additional cluster filtration may be based on cluster's size and standard deviation around cluster's centroid. The target results may therefore include: clinical preference start date, and cluster's centroids, which are the target digital feature's value.

Figure 17:
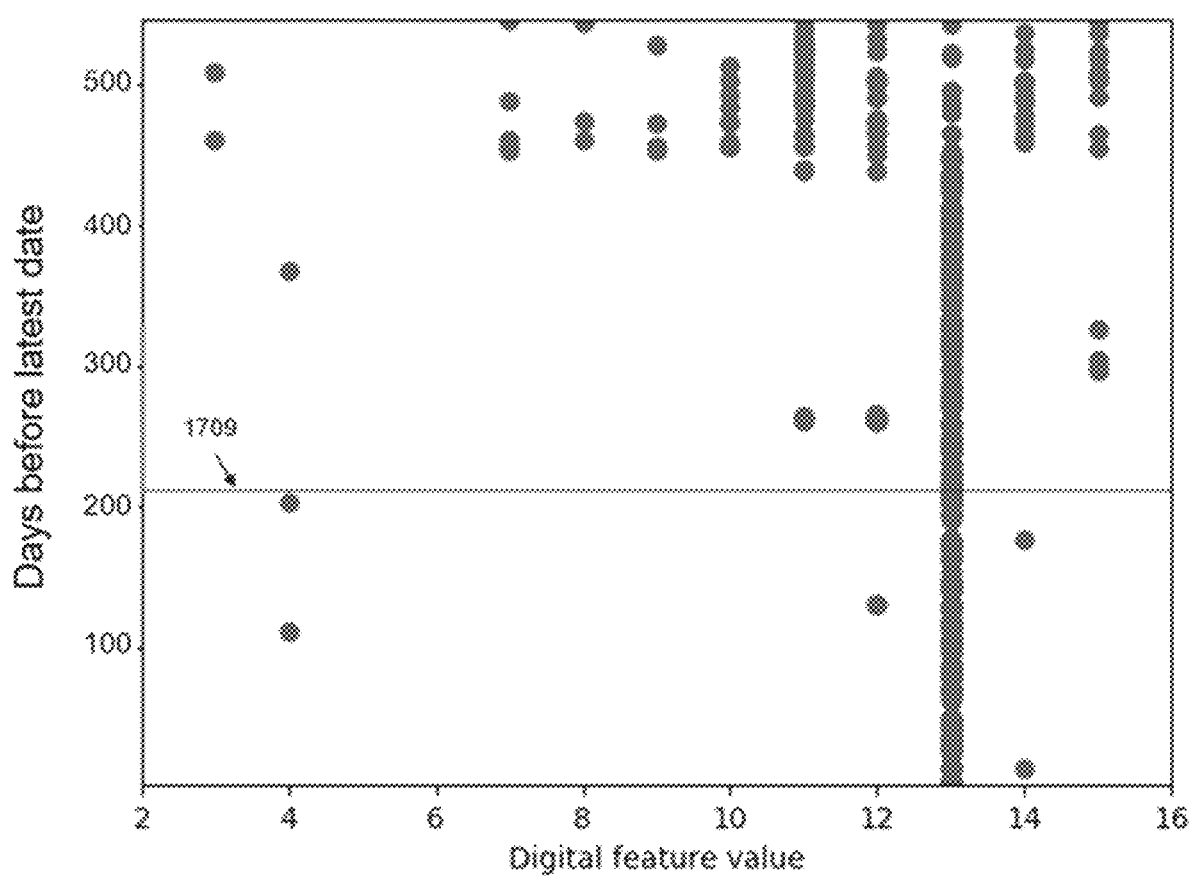
FIG. 17 illustrates one example of a statistical preference analysis for a specified user and a specified clinical behavior.

FIG. 17 shows examples of results for a digital feature of a clinical behavior. The vertical line 1709 is the found start date of the actual current clinical behavior. The final cluster was filtered with a threshold for standard deviation within cluster of <0.5. This example shows a single user ("Doctor A") as a [feature]×[timeline] graph. In this example, that Doctor A has a consistent digital clinical feature preference at stage 13, as of the date of the vertical line. In this example, the chosen period has a single clinical feature (13, corresponding to the stage an action, such as interproximal reduction, etc.) is performed, including 423 cases; this feature was consistently applied in 98.58% of all cases since the identified start of the cluster (vertical line 1790), and there was standard deviation of 0.0.

Figure 18:
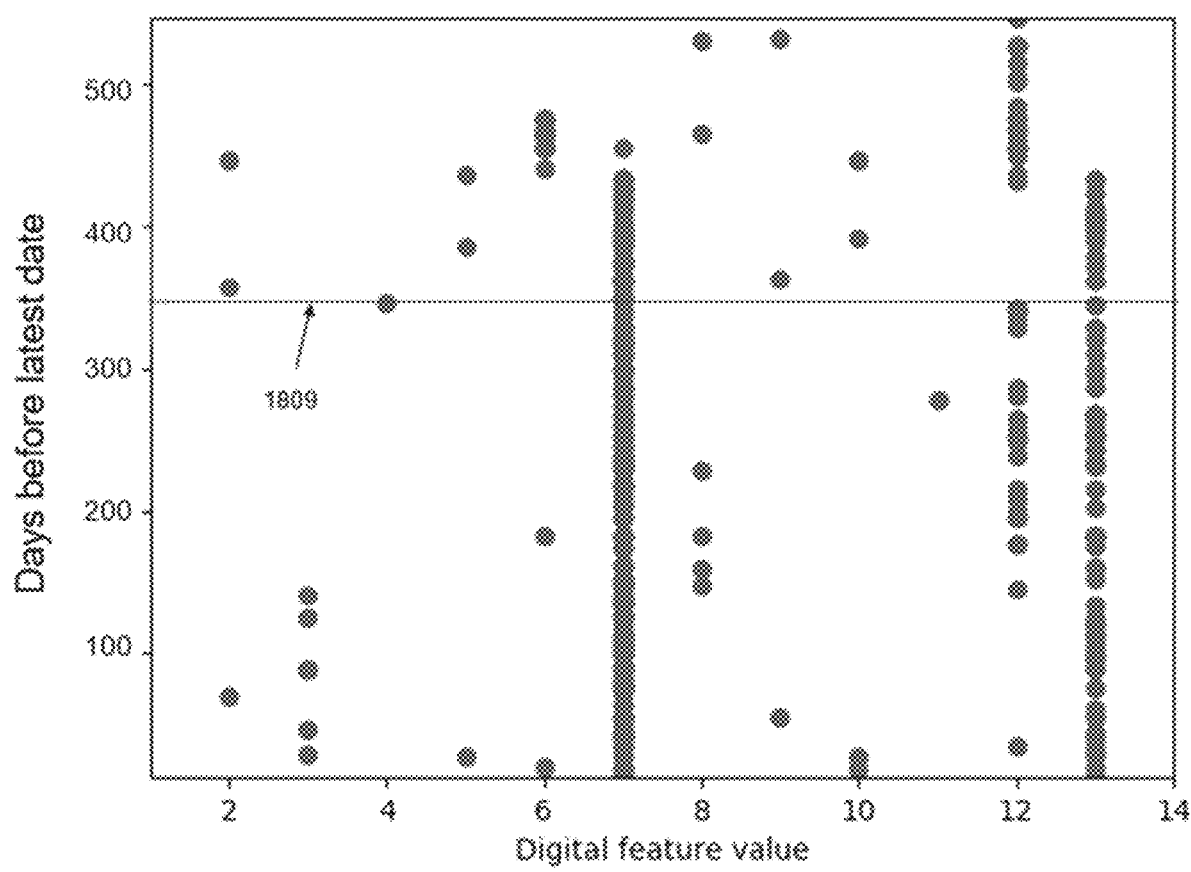
FIG. 18 is another example of a statistical preference analysis for a specified user and a specified clinical behavior.

FIG. 18 illustrates a second example for another user ("Doctor B"). In this example, Doctor B has consistent multiple preferences of digital clinical feature: 7 and 13. Doctor B's [feature]×[timeline] graph is showed on the FIG. 18. In this example, statistics for the chosen period 1809 for two clusters may be determined. The first cluster is at clinical feature 13, which includes 64 cases (17.63% of the cases since the start of the time period 1809, with a standard deviation of 0.0); the second cluster is at clinical feature 7, which includes 266 cases (73.28% of the cases since the start of the time period 1809, with a standard deviation of 0.23).

In some cases, the features may be text features that are not immediately amenable digital representation (e.g., representing as a date) for examining different clusters. Thus, it may be helpful to know what the user writes most frequent in the comments and text instructions. It may be assumed that text instructions are related to the user's clinical preferences. These preferences can change, thus it may be useful to use the most recent actual text instructions. These instructions may be filtered and normalized: to remove common phrases analysis (hello, thank you, etc.); to set all letters to the same case (e.g., capital letters in phrases are mutable and shouldn't have any impact for analysis result); to remove enumeration and list marks from instructions sequences; and/or to split long instructions at line breaks and/or periods. Text instructions may be difficult to estimate a distance metric between variations, due to phrase length difference sensitivity or cost of calculation for each-to-each relations.

In some variations, a phrase metric calculation may be estimated. As text instruction may occur less frequently, the analysis period may be split by weeks, and each text instruction frequency in this week may be calculated. This instruction frequency may be weighted by that week's weight. Thus, for each instruction there may be a vector of weekly values. Further, an instruction frequency curve may be approximated linearly using vector's values. This curve's integral may be used as an instruction metric. The apparatus or method may then determine the combination of instructions for which sum of their metrics is maximum; the number of instructions in such combinations may be limited by a top number (e.g., top 3, top 10 instructions, etc.).

Figure 19:
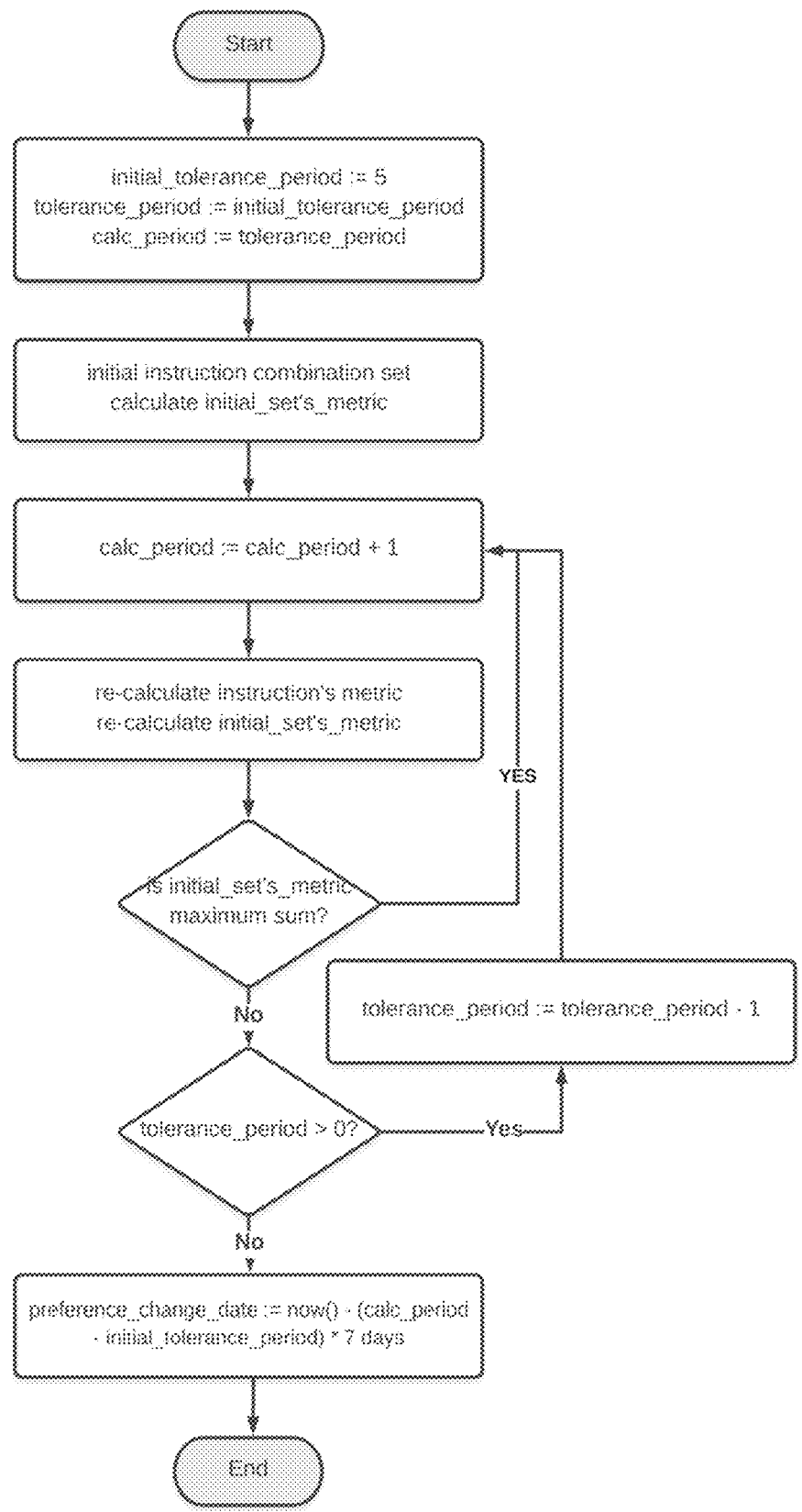
FIG. 19 is an example of a block-schema that describes one variation of a text feature definition process.

The tolerance period may be used for solving this problem. Tolerance period may be a number of weeks, during which the instruction combination set may not be changed even if its metric sum is less than the current metric's sum maximum. This may be useful when there are frequent instructions for particular case type (that isn't very common). As it was mentioned above, the tolerance period may be used to form a first set of instructions. The instruction's metric may be calculated during a tolerance period and an initial instruction's combination may be chosen using a primitive metric sort. FIG. 19 illustrates one example of a block-schema that describes an example of a text feature definition process. In FIG. 19, the method illustrated shows a method for defining a text feature by iteratively determining the maximum metric sum. In this example, the calculation period us increased by one week at each time, and all metrics are re-calculated for the new calculation period. If a chosen instruction's metric sum is a maximum, then the calculation period will be increased and the process will move forward. If the current instruction's metric sum does not reach the maximum, and the rest of tolerance period is positive, then tolerance period will be decreased, but the calculation period will be increased and process will move on. If the tolerance period is zero or negative, the process will be finished: it is assumed that preference is changed at the date, which is calculated as: now( )−(current_calculation_period−initial_tolerance_period)*7 days. In this example, the current tolerance period is 5 weeks.

The statistical preference analysis methods (and statistical preference analysis agents to perform them) described herein may be used to sharpen the data period (as shown in FIG. 17, in which only the more relevant, recent data is used). This may greatly reduce the impact of statistics noise.

EXAMPLES

Figure 20:
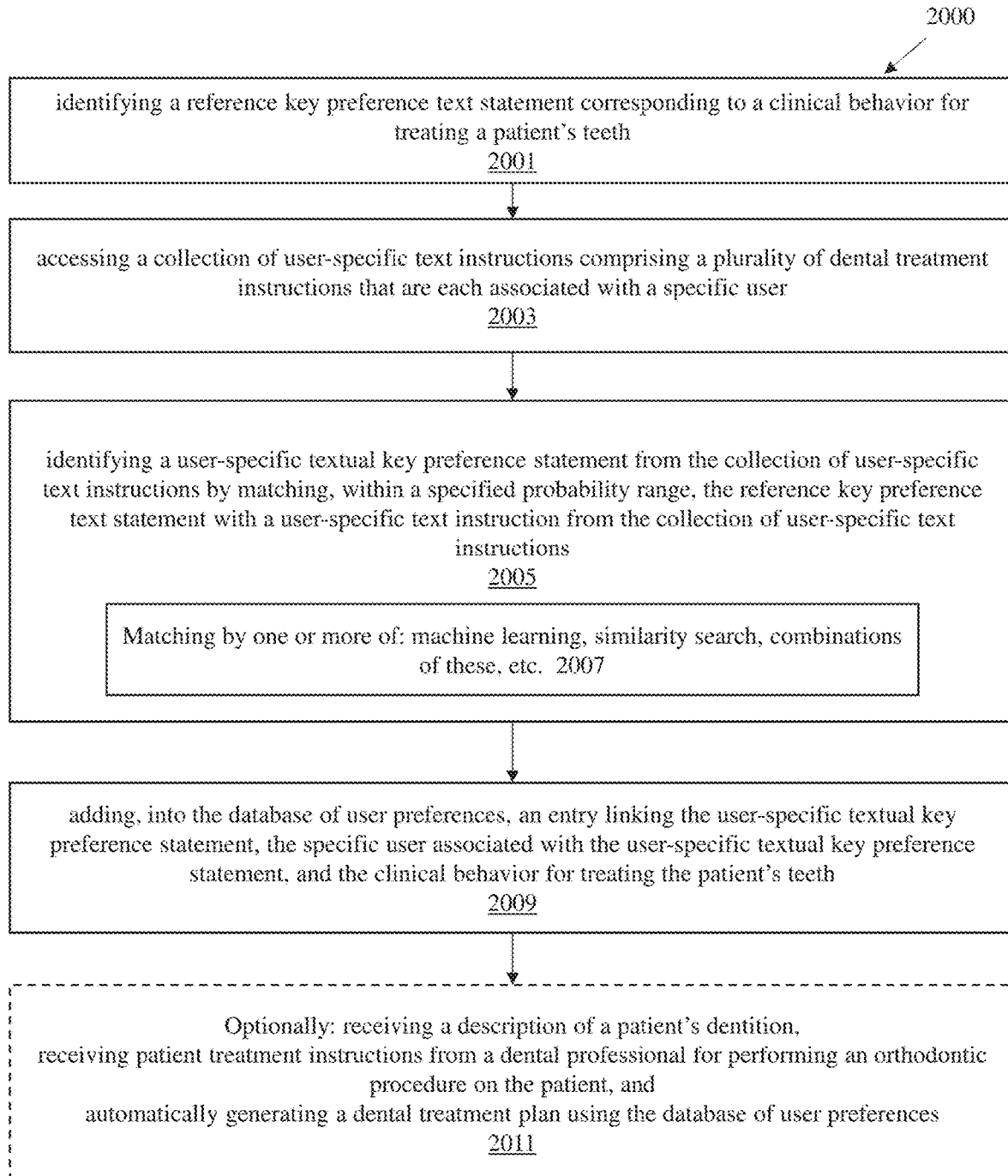
FIG. 20 illustrates one method of creating a database of user preferences.

As mentioned, described herein are methods and apparatuses for creating a database of user preferences (and/or for automatically creating a treatment plan including). For example, FIG. 20 illustrates a method 2000 for creating a database of user preferences that includes first identifying a reference key preference text statement corresponding to a clinical behavior for treating a patient's teeth 2001. The reference key preference text statement is a key preference as described above that may be used for reference when reviewing a collection of user text instructions. A collection of user-specific text instructions may be a database or collection (or derived from a database or collection) of historical treatment data. The method may then include processing such a collection of user-specific text instructions comprising a plurality of dental treatment instructions that are each associated with a specific user 2003. The collection may include data from a plurality of different users. Thereafter, a user-specific textual key preference statement may be identified from the collection of user-specific text instructions by matching, within a specified probability range, the reference key preference text statement with a user-specific text instruction from the collection of user-specific text instructions 200. The user-specific textual key preference statement may be any key preference (e.g., perform IPR at stage X, extract tooth at stage Y, etc.) in the specific user's text.

Matching refers to text matching, and may be performed by any of the methods described above, including by a machine learning agent, by a similarity search, and/or by combinations of these 2007.

Thereafter, the database of user preferences may be updated with the identified match that cross-references the specific user, the key preference (the user-specific textual key preference statement) and the associated clinical behavior for treating the patient's teeth 2009. Optionally this method of generating the database of user preferences may be included as part of a method for automatically generating a dental treatment plan, which may include the steps of receiving a description of a patient's dentition; receiving patient treatment instructions from a dental professional for performing an orthodontic procedure on the patient; and automatically generating a dental treatment plan using the database of user preferences.

Figure 21:
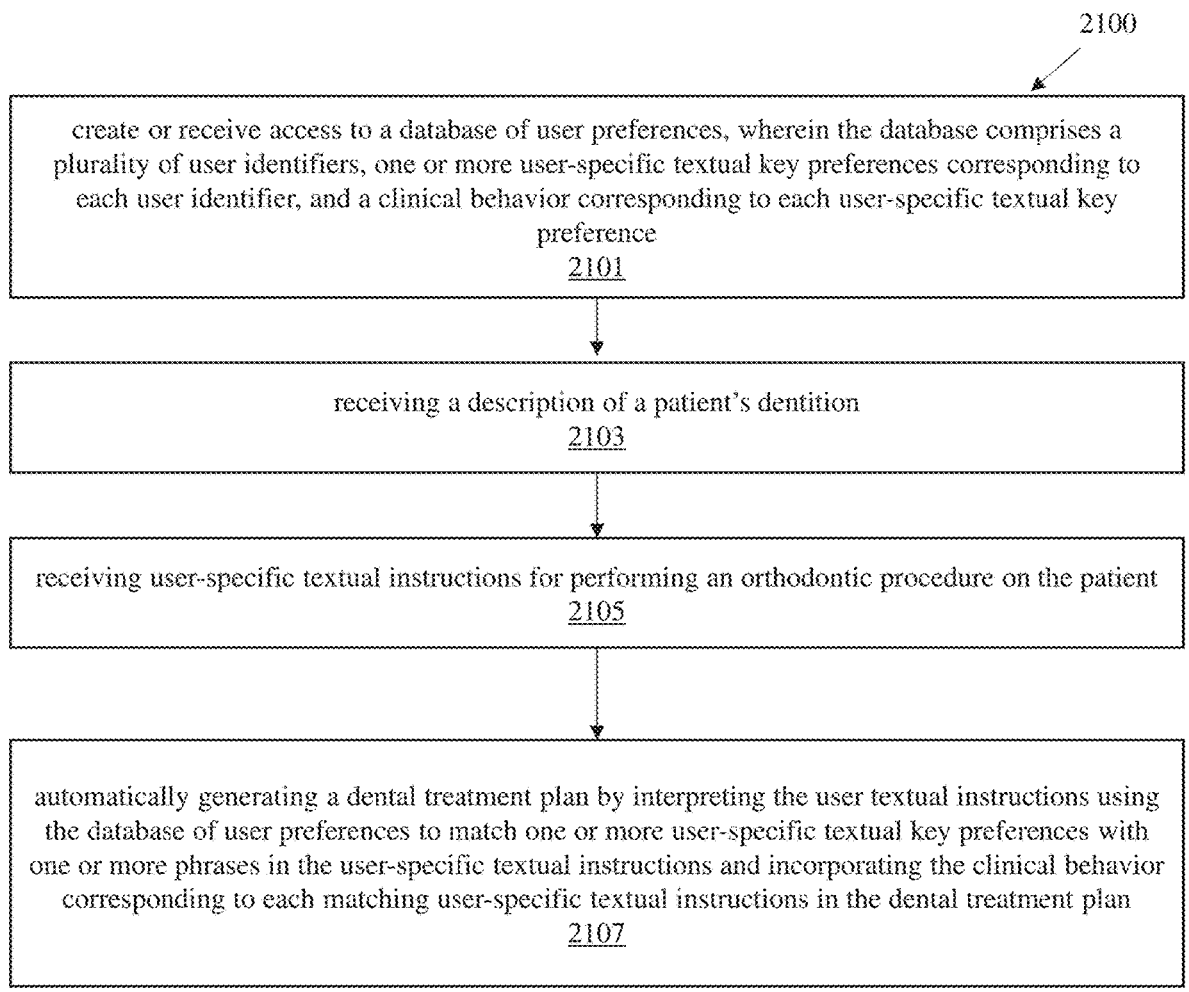
FIG. 21 illustrates a method of automatically generating a treatment plan using a database of user preferences.

FIG. 21 shows another example of a method (e.g., a computer-implemented method) for automatically generating a treatment plan using the database of user preferences. For example, in FIG. 21, the method may first create or receive access to a database of user preferences, wherein the database comprises a plurality of user identifiers, one or more user-specific textual key preferences corresponding to each user identifier, and a clinical behavior corresponding to each user-specific textual key preference 2101. A computer performing this method may then receive a request for a new treatment plan (e.g., receiving a description of a patient's dentition 2103, and receiving user-specific textual instructions for performing an orthodontic procedure on the patient 2105). Finally, a dental treatment plan may be automatically generated 2107 by interpreting the user textual instructions using the database of user preferences to match one or more user-specific textual key preferences with one or more phrases in the user-specific textual instructions and incorporating the clinical behavior corresponding to each matching user-specific textual instructions in the dental treatment plan.

Figure 22:
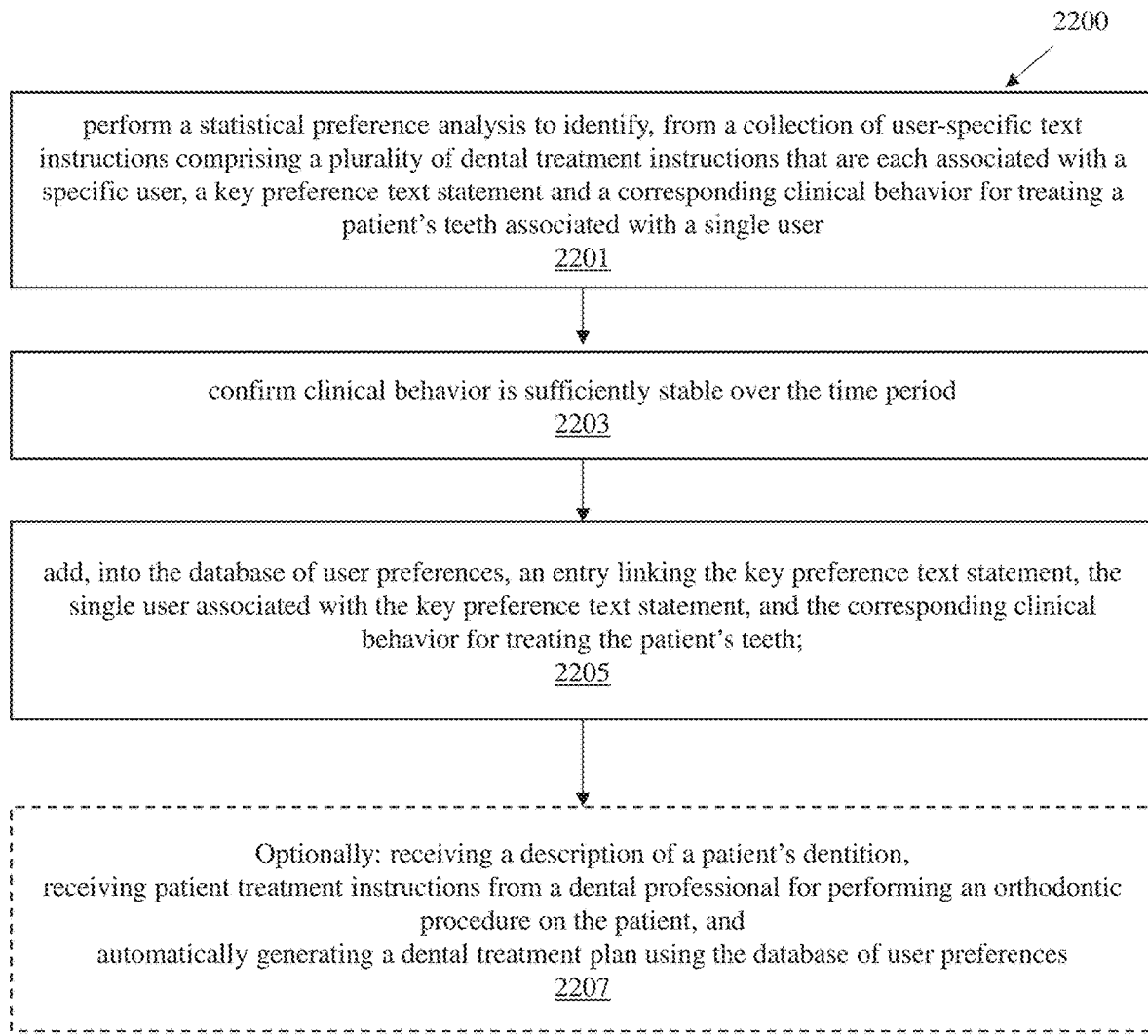
FIG. 22 illustrates another method of creating a database of user preferences.

FIG. 22 illustrates another example of a method of creating a database of user preferences. For example, in FIG. 22, the database of user preferences may be created by performing a statistical preference analysis to identify, from a collection of user-specific text instructions comprising a plurality of dental treatment instructions that are each associated with a specific user, a key preference text statement and a corresponding clinical behavior for treating a patient's teeth associated with a single user 2201. In some variations this may include determining the time period over which to perform the statistical analysis (e.g., the most recent duration during which the clinical behavior was consistent). The statistical preference analysis may be performed as descried herein, and typically is performed for a single user at a time. In instances where the clinical behavior for the single user is stable, e.g., where the same clinical behavior is used repeated over time with a very low variation, a corresponding key preference (e.g., key preference text statement) may be identified from the same user's textual instructions, and the clinical behavior, a user identifier and the corresponding key preference may be added to the database of user preferences 2205. As mentioned above, any of these methods may optionally include receiving a description of a patient's dentition, receiving patient treatment instructions from a dental professional for performing an orthodontic procedure on the patient, and automatically generating a dental treatment plan using the database of user preferences 2207.

Figure 23:
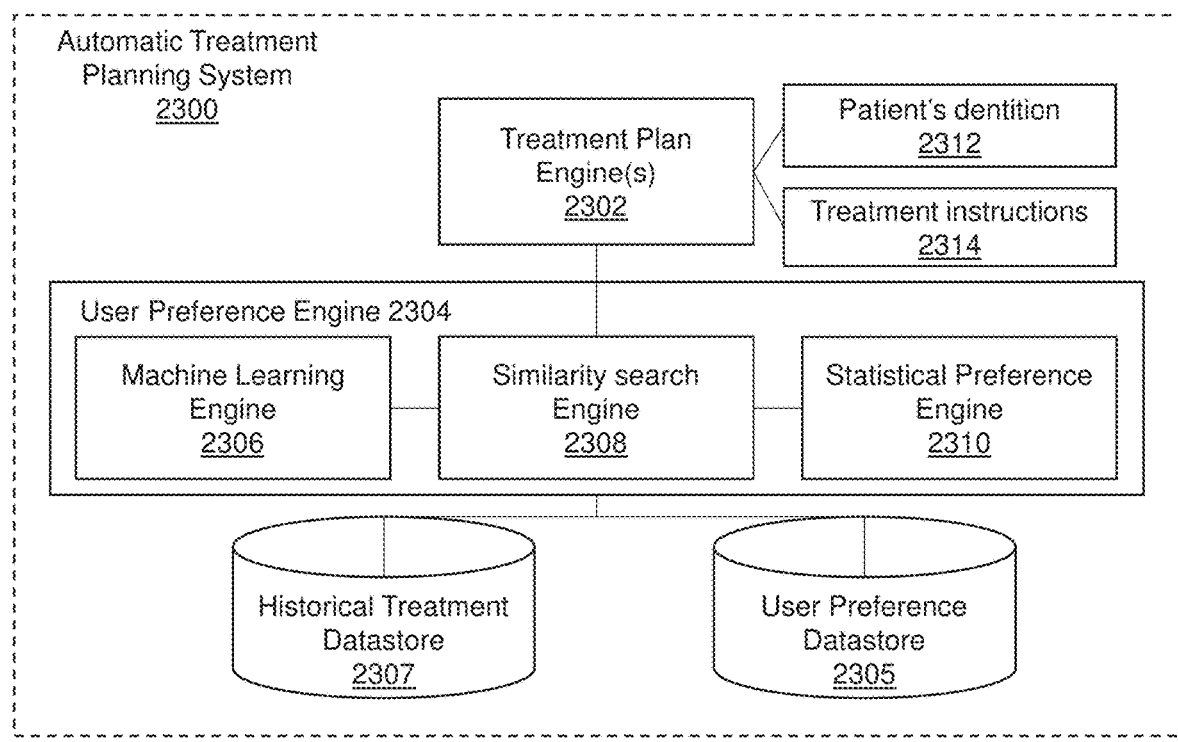
FIG. 23 shows one variation of an automatic treatment planning system as described herein.

FIG. 23 is a diagram showing an example of an automatic treatment planning system 2300, which may include as part of it a treatment planning engine 2302 and a user preference engine 2304 for generating, modifying and updating a collection of user or user group preferences (equivalently, a user preference datastore or a database of user preferences). As shown, the modules of the treatment planning system 2300 may include one or more engines and datastores. A computer system can be implemented as an engine, as part of an engine or through multiple engines. As used herein, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud based datastore is a datastore that is compatible with cloud-based computing systems and engines.

The treatment planning system 2300 may include a computer-readable medium, Treatment plan engine(s) 2302, user preference engine(s) 2304, which may include one or more machine learning engine 2306 (e.g., machine learning agent), similarity search engine 2308 (similarity search agent), and/or statistical preference engine 2310 (statistical preference agent), a historical treatment datastore 2307, an a user preference datastore 2305. One or more of the modules of the automatic treatment system 2300 may be coupled to one another (e.g., through the example couplings shown in FIG. 23) or to modules not explicitly shown in FIG. 23. The system may include a computer-readable medium that may include any computer-readable medium, including without limitation a bus, a wired network, a wireless network, or some combination thereof.

The automatic treatment planning system 2300 or any of its components may implement one or more automated agents configured, e.g., the machine learning agent/engine to learn matching of text by training as described herein. The treatment planning system may implement one or more automated agents configured to fabricate an aligner or a series of aligners. Examples of aligners are described in detail in U.S. Pat. No. 5,975,893, and in published PCT application WO 98/58596, which is herein incorporated by reference for all purposes. Systems of dental appliances employing technology described in U.S. Pat. No. 5,975,893 are commercially available from Align Technology, Inc., San Jose, Calif., under the tradename, Invisalign System. Throughout the description herein, the use of the terms "orthodontic aligner", "aligner", or "dental aligner" is synonymous with the use of the terms "appliance" and "dental appliance" in terms of dental applications. For purposes of clarity, embodiments are hereinafter described within the context of the use and application of appliances, and more specifically "dental appliances." The aligner fabrication may be part of 3D printing systems, thermoforming systems, or some combination thereof.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-implemented method comprising:
   creating a database of user preferences by:
      identifying a reference key preference text statement corresponding to a clinical behavior for treating a patient's teeth,
      accessing a collection of user-specific text instructions comprising a plurality of dental treatment instructions that are each associated with a specific user,
      identifying a user-specific textual key preference statement from the collection of user-specific text instructions by matching, within a specified probability range, the reference key preference text statement with a user-specific text instruction from the collection of user-specific text instructions, and
      adding, into the database of user preferences, an entry linking the user-specific textual key preference statement, the specific user associated with the user-specific textual key preference statement, and the clinical behavior for treating the patient's teeth;
   receiving a description of a patient's dentition;
   receiving patient treatment instructions from a dental professional for performing an orthodontic procedure on the patient; and
   automatically generating a dental treatment plan using the database of user preferences.

2. The method of claim 1, wherein automatically generating a dental treatment plan using the database of user preferences comprises finding any user-specific textual key preference statement from the database of user preferences that are associated with the dental professional, and incorporating in the dental treatment plan the clinical behavior for treating the patient's teeth that corresponds to any found user-specific key preference which matches a phrase in the patient treatment instructions.

3. The method of claim 1, wherein identifying the user-specific textual key preference statement from the collection of user-specific text instructions comprises using a machine learning agent to match the reference key preference text statement with the user-specific text instruction from the collection of user-specific text instructions.

4. The method of claim 3, further comprising training the machine learning agent using a set of positive cases selected from the plurality of dental treatment instructions and a set of negative cases selected from the plurality of dental treatment instructions.

5. The method of claim 4, wherein the machine learning agent is implementing a variation of bag of words adapted to analyze sentences.

6. The method of claim 3, wherein identifying the user-specific textual key preference statement using the machine learning agent to match the reference key preference text statement with the user-specific text instruction from the collection of user-specific text instructions further comprises using a similarity search concurrently with the machine learning agent.

7. The method of claim 6, wherein the similarity search comprises a Damerau-Levenshtein distance measure.

8. The method of claim 1, wherein identifying the user-specific textual key preference statement from the collection of user-specific text instructions comprises using a similarity search agent to match the reference key preference text statement with the user-specific text instruction from the collection of user-specific text instructions.

9. The method of claim 1, further comprising gathering the collection of user-specific text instructions from a collection of historical treatment data.

10. The method of claim 1, wherein receiving the description of a patient's dentition comprises receiving a digital model of the patient's dentition.

11. A computer-implemented method comprising:
    creating a database of user preferences by:
        identifying a reference key preference text statement corresponding to a clinical behavior for treating a patient's teeth,
        accessing a collection of user-specific text instructions comprising a plurality of dental treatment instructions that are each associated with a specific user,
        identifying a user-specific textual key preference statement from the collection of user-specific text instructions by using both a machine learning agent and similarity searching to match, within a specified probability range, the reference key preference text statement with a user-specific text instruction from the collection of user-specific text instructions, and
        adding, into the database of user preferences, an entry linking the user-specific textual key preference statement, the specific user associated with the user-specific textual key preference statement, and the clinical behavior for treating the patient's teeth;
    receiving a description of a patient's dentition;
    receiving patient treatment instructions from a dental professional for performing an orthodontic procedure on the patient; and
    automatically generating a dental treatment plan using the database of user preferences.

12. A computer-implemented method comprising:
    creating a database of user preferences, wherein the database comprises a plurality of user identifiers, one or more user-specific textual key preferences corresponding to each user identifier, and a clinical behavior corresponding to each user-specific textual key preference;
    receiving a description of a patient's dentition;
    receiving user-specific textual instructions for performing an orthodontic procedure on the patient; and
    automatically generating a dental treatment plan by interpreting the user textual instructions using the database of user preferences to match one or more user-specific textual key preferences with one or more phrases in the user-specific textual instructions and incorporating the clinical behavior corresponding to each matching user-specific textual instructions in the dental treatment plan.

13. A system comprising:
    one or more processors;
    memory coupled to the one or more processors, the memory configured to store computer-program instructions, that, when executed by the one or more processors, perform a computer-implemented method comprising:
        creating a database of user preferences by:
            identifying a reference key preference text statement corresponding to a clinical behavior for treating a patient's teeth,
            accessing a collection of user-specific text instructions comprising a plurality of dental treatment instructions that are each associated with a specific user,
            identifying a user-specific textual key preference statement from the collection of user-specific text instructions by matching, within a specified probability range, the reference key preference text statement with a user-specific text instruction from the collection of user-specific text instructions, and
            adding, into the database of user preferences, an entry linking the user-specific textual key preference statement, the specific user associated with the user-specific textual key preference statement, and the clinical behavior for treating the patient's teeth;
        receiving a description of a patient's dentition;
        receiving patient treatment instructions from a dental professional for performing an orthodontic procedure on the patient; and
        automatically generating a dental treatment plan using the database of user preferences.

14. The system of claim 13, wherein automatically generating a dental treatment plan using the database of user preferences comprises finding any user-specific textual key preference statement from the database of user preferences that are associated with the dental professional, and incorporating in the dental treatment plan the clinical behavior for treating the patient's teeth that corresponds to any found user-specific key preference which matches a phrase in the patient treatment instructions.

15. The system of claim 13, wherein identifying the user-specific textual key preference statement from the collection of user-specific text instructions comprises using a machine learning agent to match the reference key preference text statement with the user-specific text instruction from the collection of user-specific text instructions.

16. The system of claim 15, wherein the computer-implemented method further comprises training the machine learning agent using a set of positive cases selected from the plurality of dental treatment instructions and a set of negative cases selected from the plurality of dental treatment instructions.

17. The system of claim 16, wherein the machine learning agent is implementing a variation of bag of words adapted to analyze sentences.

18. The system of claim 15, wherein identifying the user-specific textual key preference statement using the machine learning agent to match the reference key preference text statement with the user-specific text instruction from the collection of user-specific text instructions further comprises using a similarity search concurrently with the machine learning agent.

19. The system of claim 18, wherein the similarity search comprises a Damerau-Levenshtein distance measure.

20. The system of claim 13, wherein identifying the user-specific textual key preference statement from the collection of user-specific text instructions comprises using a similarity search agent to match the reference key preference text statement with the user-specific text instruction from the collection of user-specific text instructions.

21. The system of claim 13, wherein the computer-implemented method further comprises gathering the collection of user-specific text instructions from a collection of historical treatment data.

22. The system of claim 13, wherein receiving the description of a patient's dentition comprises receiving a digital model of the patient's dentition.

23. A system comprising:
one or more processors;
memory coupled to the one or more processors, the memory configured to store computer-program instructions, that, when executed by the one or more processors,
perform a computer-implemented method comprising:
creating a database of user preferences by:
identifying a reference key preference text statement corresponding to a clinical behavior for treating a patient's teeth,
accessing a collection of user-specific text instructions comprising a plurality of dental treatment instructions that are each associated with a specific user,
identifying a user-specific textual key preference statement from the collection of user-specific text instructions by using both a machine learning agent and similarity searching to match, within a specified probability range, the reference key preference text statement with a user-specific text instruction from the collection of user-specific text instructions, and
adding, into the database of user preferences, an entry linking the user-specific textual key preference statement, the specific user associated with the user-specific textual key preference statement, and the clinical behavior for treating the patient's teeth;
receiving a description of a patient's dentition;
receiving patient treatment instructions from a dental professional for performing an orthodontic procedure on the patient; and
automatically generating a dental treatment plan using the database of user preferences.

24. A system comprising:
one or more processors;
memory coupled to the one or more processors, the memory configured to store computer-program instructions, that, when executed by the one or more processors, perform a computer-implemented method comprising:
creating a database of user preferences, wherein the database comprises a plurality of user identifiers, one or more user-specific textual key preferences corresponding to each user identifier, and a clinical behavior corresponding to each user-specific textual key preference;
receiving a description of a patient's dentition;
receiving user-specific textual instructions for performing an orthodontic procedure on the patient; and
automatically generating a dental treatment plan by interpreting the user textual instructions using the database of user preferences to match one or more user-specific textual key preferences with one or more phrases in the user-specific textual instructions and incorporating the clinical behavior corresponding to each matching user-specific textual instructions in the dental treatment plan.

* * * * *